US006211354B1

(12) United States Patent
Horie et al.

(10) Patent No.: US 6,211,354 B1
(45) Date of Patent: Apr. 3, 2001

(54) OPTICALLY ACTIVE DNA PROBE HAVING PHOSPHONIC DIESTER LINKAGE

(75) Inventors: Ryuichi Horie, Zama; Takahiko Ishiguro, Yokohama, both of (JP)

(73) Assignee: Tosch Corporation, Yamaguchi-ken (JP)

( * ) Notice: Subject to any disclaimer, the term of this patent is extended or adjusted under 35 U.S.C. 154(b) by 0 days.

(21) Appl. No.: 09/305,223

(22) Filed: May 5, 1999

(30) Foreign Application Priority Data

May 6, 1998 (JP) .................................................. 10-123298
Jul. 28, 1998 (JP) .................................................. 10-212569

(51) Int. Cl.[7] .................................................. C07H 21/04
(52) U.S. Cl. .................... 536/24.3; 536/25.3; 536/25.31; 536/25.32; 536/25.33; 536/25.34; 536/25.4
(58) Field of Search .................... 536/24.3, 25.3, 536/25.31, 25.32, 25.33, 25.34, 25.4, 25.6

(56) References Cited

U.S. PATENT DOCUMENTS

| 5,212,295 | * | 5/1993 | Cook et al. | .......................... 536/26.7 |
| 5,512,668 | * | 4/1996 | Stec et al. | .......................... 536/25.33 |
| 5,599,796 | * | 2/1997 | Schinazi et al. | .......................... 514/44 |
| 5,852,188 | * | 12/1998 | Cook et al. | .......................... 536/24.5 |
| 5,856,465 | * | 1/1999 | Stec et al. | .......................... 536/25.3 |
| 5,883,237 | * | 3/1999 | Stec et al. | .......................... 536/23.1 |

FOREIGN PATENT DOCUMENTS

| 0 714 986 A1 | 5/1996 | (EP) . |
| 61044353 | 4/1986 | (JP) . |
| WO 9202532 | 2/1992 | (WO) . |
| WO 9709340 | 3/1997 | (WO) . |

OTHER PUBLICATIONS

R. Horie et al; "Intercalator–linked DNA Probe Having Stereoregular 2–Aminoethyl–phosphonate Diester Linkage." Nucleic Acids Symposium Series. vol. 39. 1998, pp. 39–49, Xp002116549.

Database WPI, Section Ch, Week 8615, Derwent Publications Ltd., London, GB; Class B04, AN 86-098371, XP002116550. & JP 61 04353 A (Yuki Gosei Yakuhin Kogyo KK), Mar. 4, 1986 (1986–03–0) *Abstract*.

* cited by examiner

*Primary Examiner*—Kenneth R. Horlick
(74) *Attorney, Agent, or Firm*—Sughrue, Mion, Zinn, Macpeak & Seas, PLLC

(57) ABSTRACT

A DNA probe of the following structural formula (1) (wherein P* is an optically active phosphorus atom, each of $R_1$ and $R_2$ is a DNA oligomer having an arbitrary sequence, and $R_3$ is a fluorescent intercalative dye attached via an appropriate linker) which has an optically active configuration about P*.

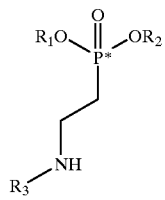

(1)

12 Claims, 18 Drawing Sheets

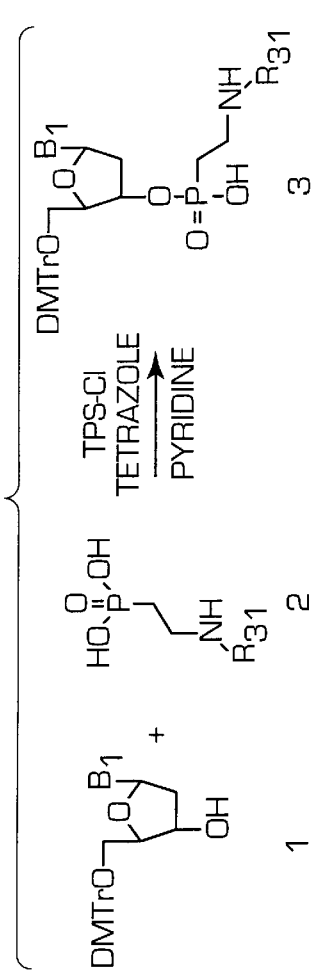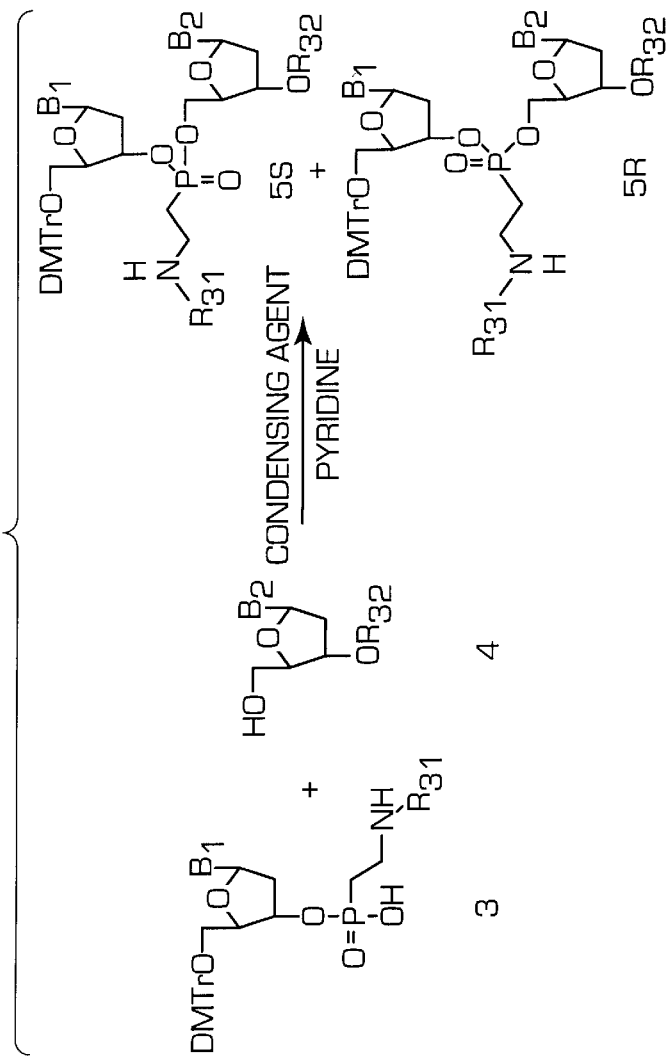
FIG. 1
FIG. 2

5
DMTr-dT-[MZ-AEP]-dC-Ac

5
DMTr-dT-[TFA-AEP]-dC-TBDMS

HPLC CHART OF YO-A13S

COLUMN: ODS-120T, Φ4.6 x 250mm (Tosoh Co., Japan)
ELUTION BUFFER: A: 5% $CH_3CN$/100mM TEAA (pH 7.0)
B: 50% $CH_3CN$/100mM TEAA (pH 7.0)
GRADIENT: B: 10% → 10% (5 MIN.) → 100% (40 MIN.)
FLOW RATE: 1ml/min
DETECTION: (UPPER) 260 nm, (LOWER) 480 nm

HPLC CHART OF YO-271S

COLUMN: ODS-120T, Φ4.6 x 250mm (Tosoh Co., Japan)
ELUTION BUFFER: A: 5% CH$_3$CN/100mM TEAA (pH 7.0)
B: 100% CH$_3$CN
GRADIENT: B: 5% → 5% (5 MIN.) → 47% (40 MIN.)
FLOW RATE: 1ml/min
DETECTION: (UPPER) 260 nm, (LOWER) 480 nm

HPLC CHART OF YO-271R

COLUMN: ODS-120T, Φ4.6 x 250mm (Tosoh Co., Japan)
ELUTION BUFFER: A: 5% $CH_3CN$/100mM TEAA (pH 7.0)
B: 100% $CH_3CN$
GRADIENT: B: 5% → 5% (5 MIN.) → 47% (40 MIN.)
FLOW RATE: 1ml/min
DETECTION: (UPPER) 260 nm, (LOWER) 480 nm COMPOUND 5S
DMTr-dC-p-dG-OTBDMS COMPOUND 12: $B_1$ = T, $B_2$ = $C^{Bz}$
COMPOUND 13: $B_1$ = $A^{Bz}$, $B_2$ = $A^{Bz}$
COMPOUND 14: $B_1$ = T, $B_2$ = $C^{Bz}$
COMPOUND 15: $B_1$ = $A^{Bz}$, $B_2$ = $A^{Bz}$

SEQUENCE LISTING

```
<160> NUMBER OF SEQ ID NOS:  4

<210> SEQ ID NO 1
<211> LENGTH: 13
<212> TYPE: DNA
<213> ORGANISM: synthetic construct
<220> FEATURE:
<221> NAME/KEY: misc_feature
<222> LOCATION: (5)..(6)
<223> OTHER INFORMATION: Between positions 5 and 6, a phosphonic diester
      linkage is indicated (see page 21, line 12-13 and
      lines 21-22 of the specification)

<400> SEQUENCE: 1
aaaaaaaaaa aaa                                                           13

<210> SEQ ID NO 2
<211> LENGTH: 13
<212> TYPE: DNA
<213> ORGANISM: synthetic construct
<220> FEATURE:
<221> NAME/KEY: misc_feature
<222> LOCATION: (5)..(6)
<223> OTHER INFORMATION: Between positions 5 and 6, a phosphonic diester
      linkage is indicated (see page 22, lines 5-6 and
      24-25)

<400> SEQUENCE: 2
ctcgcggggg ctg                                                           13

<210> SEQ ID NO 3
<211> LENGTH: 13
<212> TYPE: DNA
<213> ORGANISM: synthetic construct

<400> SEQUENCE: 3
ctcgcggggg ctg                                                           13

<210> SEQ ID NO 4
```

-continued

```
<211> LENGTH: 13
<212> TYPE: DNA
<213> ORGANISM: synthetic construct

<400> SEQUENCE: 4
gtgcccccgc gag                                                        13
```

OPTICALLY ACTIVE DNA PROBE HAVING PHOSPHONIC DIESTER LINKAGE

The present invention relates to a DNA probe having an optically active phosphonic diester linkage and a method of its preparation. The present invention also relates to a method of selective cleavage of a trialkylsilyl ether linkage used for preparing the DNA probe, particularly to a method of selective elimination of a trialkylsilyl group as a hydroxyl-protecting group. The oligonucleotide obtained according to the present invention can be used for identification, extraction and control of expression of a target gene in the fields such as genetic engineering, clinical diagnosis and medical treatment.

In detection and quantification of a target nucleic acid, the ability of the target nucleic acid to hybridize with a nucleic acid probe having a base sequence complementary to a specific nucleotide sequence, namely a specific base sequence in the target nucleic acid is utilized.

On the other hand, intercalative dyes such as oxazole yellow, thiazole orange and ethidium bromide are known to remarkably enhance the fluorescence upon binding to a double-stranded nucleic acid.

Using this property, the present inventors invented a method of assay of a nucleic acid containing a specific nucleic acid sequence (a target nucleic acid) by detecting the specific nucleic acid sequence, which comprises a step of adding a single-stranded oligonucleotide containing a nucleic acid sequence complementary to the specific nucleic acid sequence in the target nucleic acid as a probe to a sample and hybridizing the probe with the target nucleic acid, wherein the probe is a single-stranded oligonucleotide labeled with a fluorescent intercalative dye which intercalates into the hybrid of the target nucleic acid and the single-stranded oligonucleotide (JP-A-8-211050, U.S. Pat. No. 5,814,447 and EP 714986).

The above-mentioned invention provided a labeled nucleic acid probe for homogeneous and simple one-step detection of a nucleic acid containing a specific nucleic acid sequence which enabled detection of hybridization or quantification of the resultant hybrid without the necessity of a step of separating the unhybridized excess probe in detection of a target nucleic acid.

When an intercalator as a label was attached in the middle of a nucleic acid probe via an aminoalkylphosphonate linker having no influence on the hybridization with the target nucleic acid, it was possible to detect even one base substitution in a target nucleic acid, though the method of labeling the nucleic acid probe is not limited thereto.

A phosphonic diester linkage as an inter-nucleotide linkage has a chiral center on the phosphorus atom in it. Namely, a DNA probe obtained by introducing phosphonic acid in the middle of an oligonucleotide has two stereoisomers having R- and S-absolute configurations.

Antisense DNA containing methylphosphoric acid under extensive research as a gene drug is known to vary in stability of its hybridization with a complementary strand (Tm), conformation and reactivity with nucleases, depending on the absolute configuration of the methylphosphonic acid.

The object of the present invention is to provide a nucleic acid probe having an intercalator as a label attaching in the middle of the nucleic acid sequence via an aminoalkylphosphonate linker, which has a configurationally different phosphorus atom.

As a result of extensive research with a view to attaining this object, the present inventors have accomplished the present invention. Namely, the present invention provides an optically active DNA probe and a method of its preparation, wherein the nucleic acid probe has an intercalator as a label attaching in the middle of the nucleic acid sequence via a chiral aminoalkylphosphonate linker.

The present invention also provides an optically active phosphonic dinucleotide useful as a precursor for preparation of the optically active DNA probe and a method of its preparation. The present inventors have found that a phosphonic dinucleotide obtained in the form of a racemate can show an Rf difference between its stereoisomers depending on the type of the protecting group in it. On the basis of this discovery, they resolved the stereoisomers easily and established a method of preparing an optically active phosphonic dinucleotide.

FIG. 1 illustrates the process of Example 1.
FIG. 2 illustrates the process of Example 2.
FIG. 3 is the NMR chart of Compound 5.
FIG. 4 is the NMR charts of Compounds 5S and 5R.
FIG. 5 is the NMR charts of Compounds 5S and 5R.
FIG. 6 illustrates the details of Compounds 5S/5R ($B_1$=T, $B_2=C^{Bz}$, $R_{31}$=MZ, $R_{32}$=Ac) and 5S/R ($B_1$=T, $B_2=C^{Bz}$, $R_{31}$=TFA, $R_{32}$=TBDMS).
FIG. 7 illustrates the process of Example 3.
FIG. 8 illustrates the process of Example 3.
FIG. 9 illustrates the process of Example 4.
FIG. 10 illustrates the process of Example 5.
FIG. 11 illustrates the DNA probe according to the present invention obtained in Example 8.
FIG. 12 is the HPLC chart of the DNA probe according to the present invention obtained in Example 8.
FIG. 13 illustrates the DNA probe according to the present invention obtained in Example 9.
FIG. 14 is the HPLC chart of the DNA probe according to the present invention obtained in Example 9.
FIG. 15 illustrates the process of Examples 10 and 11.
FIG. 16 illustrates the DNA probe according to the present invention obtianed in Example 14.
FIG. 17 is the HPLC chart of the DNA probe according to the present invention obtained in Example 14.
FIG. 18 illustrates the DNA probe according to the present invention obtained in Example 15.
FIG. 19 is the HPLC chart of the DNA probe according to the present invention obtained in Example 15.
FIG. 20(A) shows the fluorescence spectrum of an aqueous solution containing the DNA probe YO-A13S obtained in Example 8 and the target nucleotide oligo-dT (30 mer) measured under hybridizable conditions (I), the fluorescence spectrum of an aqueous solution containing the DNA probe YO-A13R obtained in Example 9 and the target nucleotide oligo-dT (30 mer) measured under hybridizable conditions (II), the fluorescence spectrum of YO-A13R in an aqueous solution (III) and the fluorescence spectrum of YO-A13S in an aqueous solution (IV).
FIG. 20(B) shows the fluorescence spectra of aqueous solutions containing the DNA probe YO-A13S or YO-A13R obtained in Example 8 or 9 and oligo-dA (30 mer).
FIG. 20(C) shows the fluorescence spectra of aqueous solutions containing the DNA probe YO-A13S or YO-A13R obtained in Example 8 or 9 and a recombinant HCV RNA.
FIG. 21(A) show the fluorescence spectrum of an aqueous solution containing the DNA probe YO-271S obtained in Example 14 and the target nucleic acid Temp271 measured under hybridizable conditions (Temp271) and the fluorescence spectrum of YO-271S in aqueous solution (none).
FIG. 21(B) show the fluorescence spectrum of an aqueous solution containing the DNA probe YO-271R obtained in Example 15 and the target nucleic acid Temp271 measured under hybridizable conditions (Temp271) and the fluorescence spectrum of YO-271R in aqueous solution (none).

Figure 3:
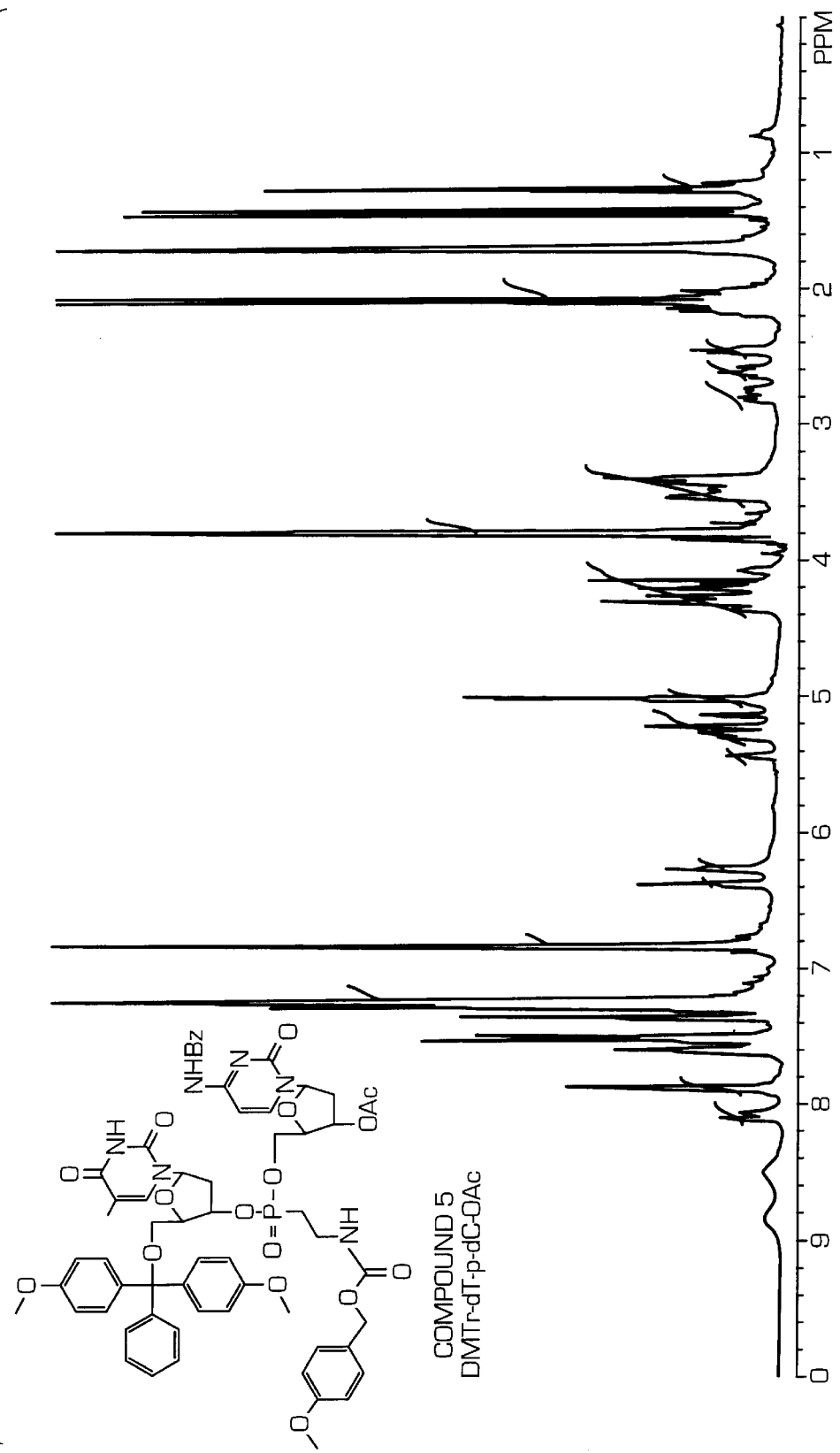

Now, the present invention will be described in detail. A nucleosides of the following structural formula (10) is used as a starting material in the present invention, and those wherein $R_{21}$ is a DMTr (4,4'-dimethoxytrityl) group are obtainable by the method disclosed in the literature (J. Am. Chem. Soc., vol.84, 430 (1962)). Such compounds on the market may also be used.

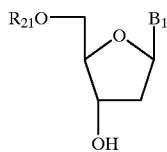
(10)

Further, a compound of the following formula (11) obtainable by protecting commercially available 2-aminoethylphosphonic acid with an appropriate amino-protecting group is used. The amino-protecting group may a commonly used protecting group such as Z (benzyloxycarbonyl), MZ (4-methoxybenzyloxycarbonyl), Fmoc (9-fluorenylmethoxycarbonyl), TFA (trifluoroacetyl) and Bz (benzoyl), but preferably a protecting group which is not eliminated under the same conditions as a DMTr group is eliminated.

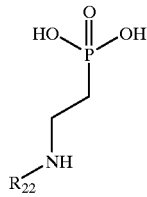
(11)

Dehydration condensation of a compound of the structural formula (10) and a compound of the structural formula (11) gives a compound of the following structural formula (12). Although the condensation agent used for the condensation is not limited, it is usually an agent capable of forming a phosphoric ester such as dicyclohexylcarbodiimide, alkylbenzenesulfonic acid derivatives and bis(2-oxo-3-oxazolidinyl)phosphinic chloride. As the solvent, a polar solvent which dissolves the reaction product such as acetonitrile and pyridine may be used. The reaction temperature is not particularly limited either, but it is from the melting point to the boiling point of the solvent, preferably from −10° C. to 60° C.

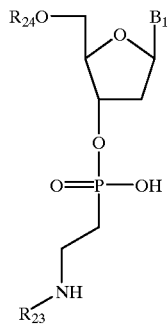
(12)

The resulting compound of the structural formula (12) is condensed with a nucleoside of the following structural formula (6) having an unprotected hydroxyl group at the 5'-position to give a phosphonic dinucleotide of the following structural formula (7). As the protecting group at the 3'-position of the compound of structural formula (6), a hydroxyl-protecting group such as Ac (acetyl), Bz, TBDMS (tert-butyldimethylsilyl) or Bn (benzyl), preferably a group which is not eliminated under the same condition as a DMTr group and the protecting group for the amino group in aminoethylphosphonate may be used.

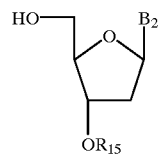
(6)

(7)

Although the condensation agent used for the condensation is not limited, it is usually an agent capable of forming a phosphoric ester such as dicyclohexylcarbodiimide, alkylbenzenesulfonic acid derivatives and bis(2-oxo-3-oxazolidinyl)phosphinic chloride. As the solvent, a polar solvent which dissolves the reaction product such as acetonitrile and pyridine may be used. The reaction temperature is not particularly limited either, but it is from the melting point to the boiling point of the solvent, preferably from −10° C. to 60° C.

This compound has a chiral center on the phosphorus atom and is obtained as a mixture of the two stereoisomers having R- and S-configurations. The stereoisomers can be optically resolved by conventional techniques for purificatory separation of compounds such as silica gel column chromatography and reverse phase column chromatography.

In an attempt to separate the stereoisomers, the present inventors have found that there is difference in Rf between the two stereoisomers depending on the kind of the protecting group at the 3'-position of the phosphonic dinucleotide. When the amino-protecting group is a MZ group, and the protecting group at the 3'-position is Ac, the two stereoisomers have the same Rf and are difficult to separate. However, when the amino-protecting group is a TFA group, and the protecting group at the 3'-position is a TBDMS group, the difference in Rf between the two stereoisomers is large enough to facilitate their separation. The absolute configurations of the resolved stereoisomers are determined by analytical methods such as $^1$H NMR and $^{31}$P NMR.

Then, the resolved optically active phosphonate dinucleotide is subjected to deprotection of the 3'-position. The deprotection is preferably carried out under such conditions that any other protecting groups in the compound are not eliminated. A trialkylsilyl ether such as a TBDMS group, which is preferable as the protecting group at the 3'-position as described above, is excellent as a protecting group for an alcoholic hydroxyl group, and its greatest advantage is that it can be eliminated by using fluoride anion (tetrabutylammonium fluoride, n-Bu$_4$NF) under neutral conditions. If the substrate has a functional group vulnerable to basicity, the substrate can decompose under such conditions. In such a case, addition of acetic acid to the reaction system is known to afford more selective elimination of the silyl ether by moderating the basicity of tetrabutylammonium fluoride (K. K. Ogilvie and S. L. Beaucage, Tetrahedron Lett. (1976) 1255–1256). This conventional method can be employed in the present invention for deprotection of the 3'-position. However, when the substrate has a functional group unstable against both acidity and basicity, it is preferred to do as described below in order to more accurately and selectively eliminate a trialkylsilyl ether such as a TBDMS group only without acid or base.

Namely, when a trialkylsilyl ether as a protecting group in a compound having a functional group unstable against both acidity and basicity is eliminated by using tetrabutylammonium fluoride, addition of both acetic acid and an amine can moderate both acidity and basicity. The amine to be added is not particularly limited, but it is preferably an amine which can be removed after the reaction by distillation or the like such as triethylamine. With respect to the method of their addition, acetic acid and an amine may be added as such or as an aqueous solution such as an triethylamine-acetate buffer. In either case, the addition of acetic acid and an amine does not stop the reaction to eliminate the trialkylsilyl ether linkage It is preferred to add a mixture of acetic acid and triethylamine with a tetrabutylammonium fluoride solution is added to the substrate solution rather than add a tetrabutylammonium fluoride solution to a mixture of acetic acid and triethylamine with the substrate solution, because the acidity and basicity of tetrabuthylammonium fluoride can be moderated more effectively.

Though there is no restriction on the amounts of tetrabuthylammonium fluoride, acetic acid and triethylamine to be added, the amount of tetrabutylammonium fluoride to be used is, for example, from 1 to 10 times, preferably from 1.5 to 3 times, as great as that of the substrate. In the TBDMS-eliminating reaction of tetrabutylammonium fluoride, addition of acetic acid and triethylamine delays disappearance of the starting material, but the reaction finishes in about one or two hours when the molar ratio of tetrabutylammonium fluoride:acetic acid:triethylamine is 2:1:1.

The above-mentioned method of eliminating a trialkylsilyl ether as a protecting group is effective especially for elimination of the TBDMS group preferable as the protecting group at the 3'-position of the above mentioned compound. According to a report by the present inventors, conventional treatment of a compound of the following structural formula (15) with tetrabutylammonium fluoride alone in THF gave the intended product of the following structural formula (16) in a yield of about 37% after isolation. TLC analysis of the reaction solution demonstrated disappearance of the starting material but identified decomposition products such as DMTr group in addition to the intended product. On the other hand, when acetic acid and triethylamine were added as a triethylamine-acetate buffer to a THF solution of the starting material, the yield of the intended product after isolation increased due to decrease of decomposition products The results were confirmed irrespective of the kinds of the bases in the nucleic acids.

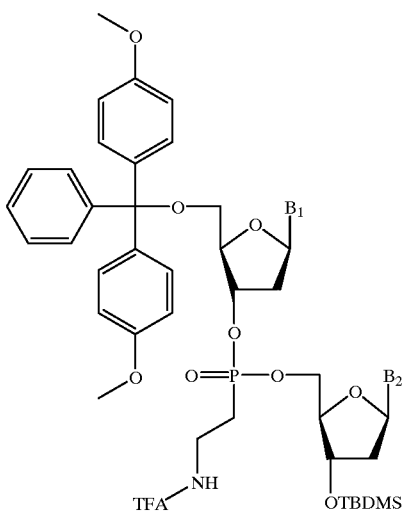

(15)

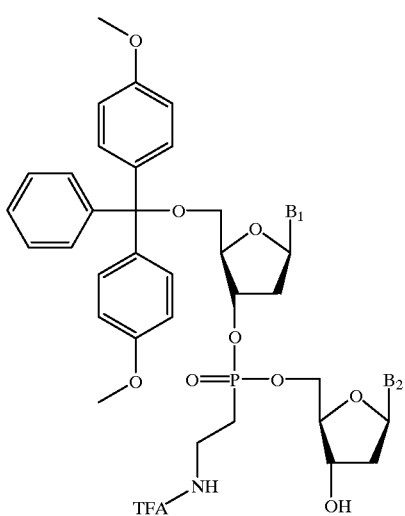

(16)

The 3'-hydroxyl group thus formed may be subjected to phosphorylation or phosphoroamiditation and then introduced to the 5'-end of the a separately prepared DNA oligomer. Further, the DNA oligomer having the introduced phosphonic acid dinucleotide at the 5'-end may be elongated to give an oligomer having an intended sequence. The DNA oligomer can be obtained by conventional methods for preparation of DNA oligomers such as a liquid phase method or a solid phase method. Phosphoroamiditation of a phosphonic dinucleotide makes it possible to handle the phosphonic dinucleotide in the same manner as commercially available reagents for DNA synthesizers. DNA synthesis using a phosphoroamiditated phosphonic dinucleotide by a DNA synthesizer affords a DNA oligomer having a phosphonic diester at an arbitrary position of the DNA sequence.

Finally, the phosphonic oligomer thus obtained is deprotected, and an intercalative dye is attached to the deprotected amino group in the aminoethylphosphonate to give the optically active DNA probe of the present invention.

Use of an intercalative dye having a functional group which can directly attach to an amino group facilitates attachment of an intercalative dye to the amino group. When a bifunctional reagent having functional groups at both ends such as N-succinimidyl-3-(2-pyridyldithio)propionate (SPDP) and as N-succinimidyl-6-maleimidohexanoate (EMCS) is bonded to the amino group in the aminoethylphosphonate, and an intercalative dye is attached via the bifuctional reagent, it is possible to arbitrarily select the functional group in the intercalative dye.

As the intercalative dye, any compound which is known to remarkably alter the fluorescence on intercalation into a double-strand nucleic acid such as oxazole yellow, thizole orange and ethiduim bromide may be used without restriction. Particularly, those which remarkably enhances the fluorescence intensity are preferable. As examples of such intercalative dyes, thiazol orange and oxazole yellow may be mentioned.

Now, the present invention will be described in further detail with reference to Examples. However, the present invention is by no means restricted to those specific Examples.

The symbols used in the Examples have the following meanings.

T: thymine
$A^{Bz}$: N-benzoyl-adenine
$C^{Bz}$: N-benzoyl-cytosine
$G^{iBu}$: N-isobutyryl-guanine
MZ: 4-methoxybenzyloxycarbonyl
TFA: trifluoroacetyl
Ac: acetyl
TBDMS: tert-butyldimethylsilyl

EXAMPLE 1

As shown in FIG. 1, Compound 1 and Compound 2 were mixed in the ratios shown in Table 1 and dissolved in pyridine, and triisopropylbenzenesulfonyl chloride (TPS-Cl) and tetrazole in pyridine were added dropwise. The reaction solution was stirred at 40° C. for 4 hours. Then, 50% aqueous pyridine was added, and the pH was adjusted to about 7.0 with saturated aqueous sodium bicarbonate. The reaction solution was partitioned between ethyl acetate and saturated aqueous sodium chloride, and the organic layer was dried and concentrated in vacuo. Purification of the concentrate by silica gel column chromatography gave Compound 3 in the amounts and yields shown in Table 1.

TABLE 1

| Compound 1 | | Compound 2 | | TPS-Cl equiv-alent | Tetra-zole equiv-alent | Compound 3 | |
|---|---|---|---|---|---|---|---|
| $B_1$ | mol | $R_{31}$ | Equivalent | alent | alent | Amount | Yield |
| T | 0.099 mmol | MZ | 2 eq. | 4 eq. | 12 eq. | 0.050 mmol | 51% |
| T | 0.092 mmol | TFA | 2 eq. | 4 eq. | 12 eq. | 0.070 mmol | 76% |
| $A^{Bz}$ | 0.151 mmol | TFA | 2 eq. | 4 eq. | 12 eq. | 0.086 mmol | 52% |
| $C^{Bz}$ | 1.58 mmol | TFA | 1.6 eq. | 3.2 eq. | 9.5 eq. | 1.098 mmol | 70% |

EXAMPLE 2

As shown in FIG. 2, Compound 3 and Compound 4 were mixed in the ratios shown in Table 2 and dissolved in pyridine. A condensation agent (triisopropylbenzenesulfonyl chloride (TPS-Cl), triisopropylbenzenesulfonyl-3-nitrotriazole (TPS-Ntriazole) or bis(2-oxo-3-oxazolidinyl) phosphinic chloride (BOP-Cl)) was added, and the reaction was carried out at 40° C. After the reaction times shown in Table 2, 50% aqueous pyridine was added, and the pH was adjusted to about 7.0. The reaction solution was partitioned between ethyl acetate and saturated aqueous sodium chloride, and the organic layer was dried and concentrated in vacuo. Purification of the concentrate by silica gel column chromatography gave Compound 5S and Compound 5R in the amounts and yields shown in Table 2.

HPTLC plate) and a 95:5 mixture of chloroform and methanol as a developing solvent were used.

EXAMPLE 3

Figure 7:
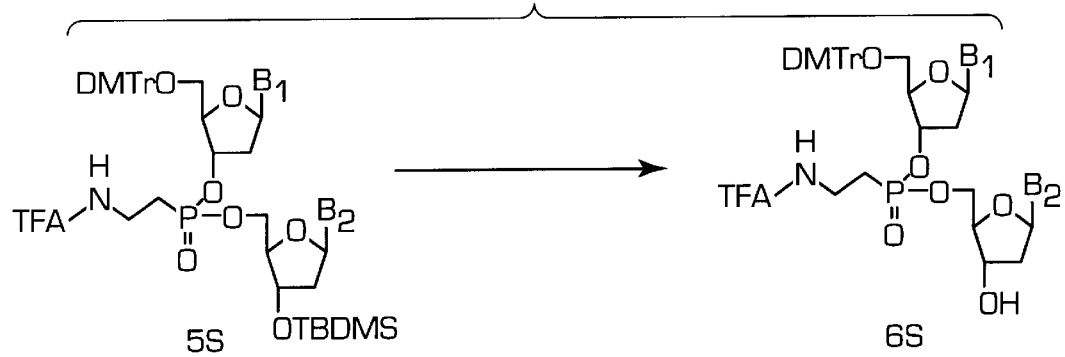
Figure 8:
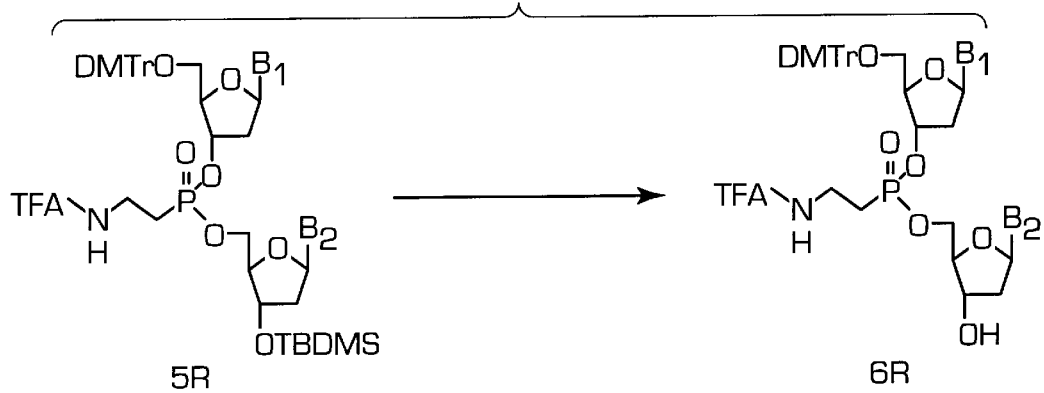

As shown FIG. 7 and FIG. 8, 0.1 M tetrabutylammonium fluoride in THF was added dropwise to Compound 5R or 5S in THF. After 2 hours of stirring, the resulting reaction solution was concentrated to dryness in vacuo. The residue was partitioned between chloroform and saturated aqueous sodium chloride, and the organic layer was dried and concentrated to dryness. Purification of the residue by silica gel column chromatography gave Compound 6S or Compound 6R.

TABLE 2

| Compound 3 | | Compound 4 | | | | Reaction | | Compound 5 | |
|---|---|---|---|---|---|---|---|---|---|
| $B_1$ | $R_{31}$ | $B_2$ | $R_{32}$ | Equivalent | Condensation agent | time | Rf value*[1] | | yield |
| T | MZ | $C^{Bz}$ | Ac | 1 eq. | TPS-Cl | 3 days | R = S = 0.27 | | 12% (R + S) |
| T | TFA | $C^{Bz}$ | TBDMS | 1 eq. | TPS-Cl | 2 days | R = 0.29 | | 6% (R + S) |
| T | TFA | $C^{Bz}$ | TBDMS | 1 eq. | TPS-NTriazole | 2 days | S = 0.39 | | 12% (R + S) |
| | | | | | | | | | 21% (5S) |
| T | TFA | $C^{Bz}$ | TBDMS | 1 eq. | BOP-Cl | 5 hours | | | 24% (R + S) |
| $A^{Bz}$ | TFA | $A^{Bz}$ | TBDMS | 2 eq. | BOP-Cl | 2.5 hours | R = 0.29 | | 35% (5R) |
| | | | | | | | S = 0.37 | | 12% (R + S) |
| | | | | | | | | | 31% (5R) |
| $C^{Bz}$ | TFA | $G^{iBu}$ | TBDMS | 1.25 eq. | BOP-Cl | 2.5 hours | R = 0.23 | | 42% (5S) |
| | | | | | | | S = 0.35 | | 51% (5R) |

*[1]TLC conditions Merck Silica gel 60 $F_{254}$ HPTLC plate
Developing Solvent 95:5 Chloroform-Methanol From comparison of the proton NMR spectra of the two stereoisomers, the one which shifted the P-CH$_2$ peak (P-1 position) to a higher magnetic field was designated as 5S, and the one which shifted the corresponding peak to a lower magnetic field was designated as 5R.

The NMR (CDCl$_3$) chart of Compound 5(R+S) ($B_1$=T, $B_2$=$C^{Bz}$, $R_{31}$=MZ, $R_{32}$=Ac) at 500 MHz is shown in FIG. 3.

Figure 4:
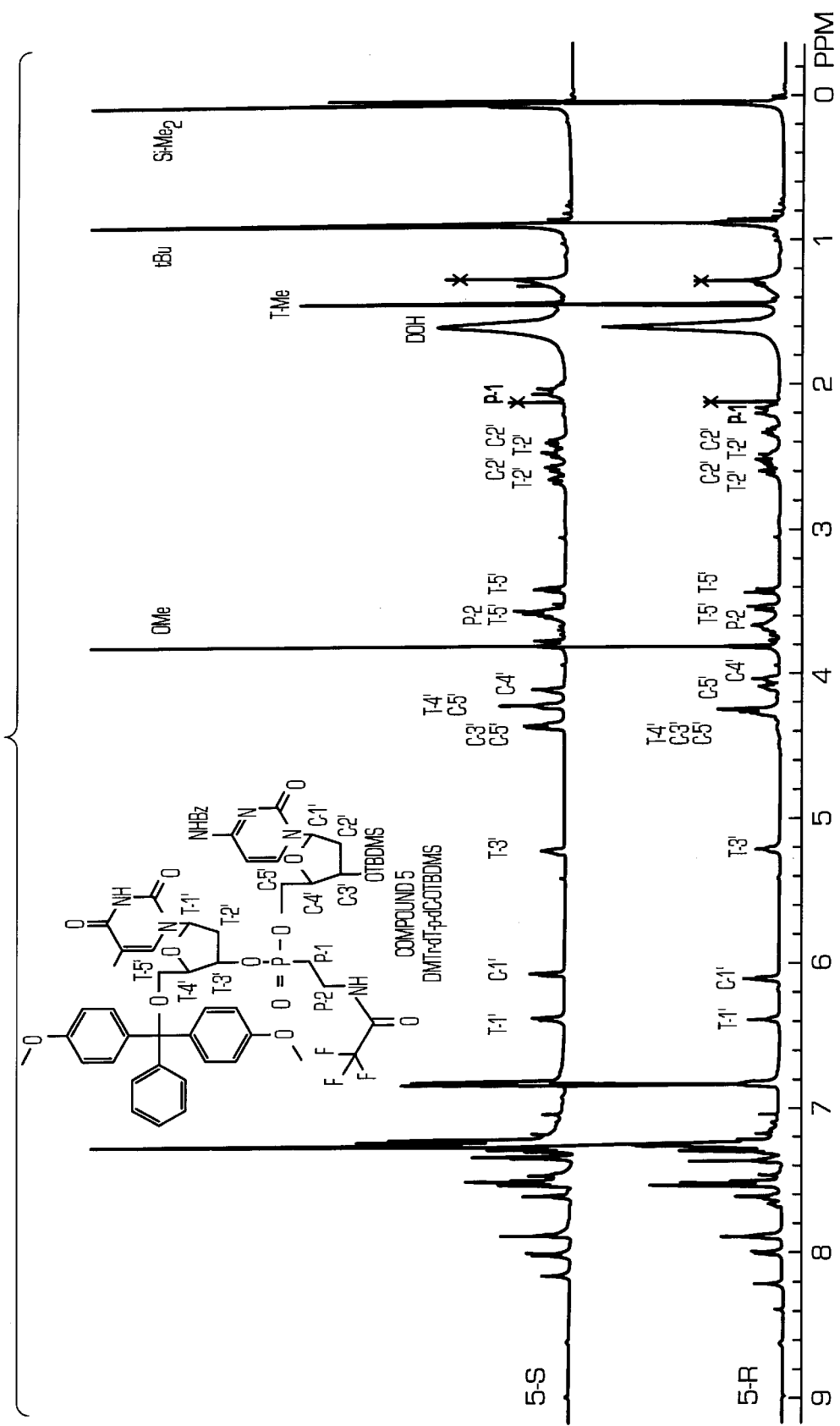
Figure 5:
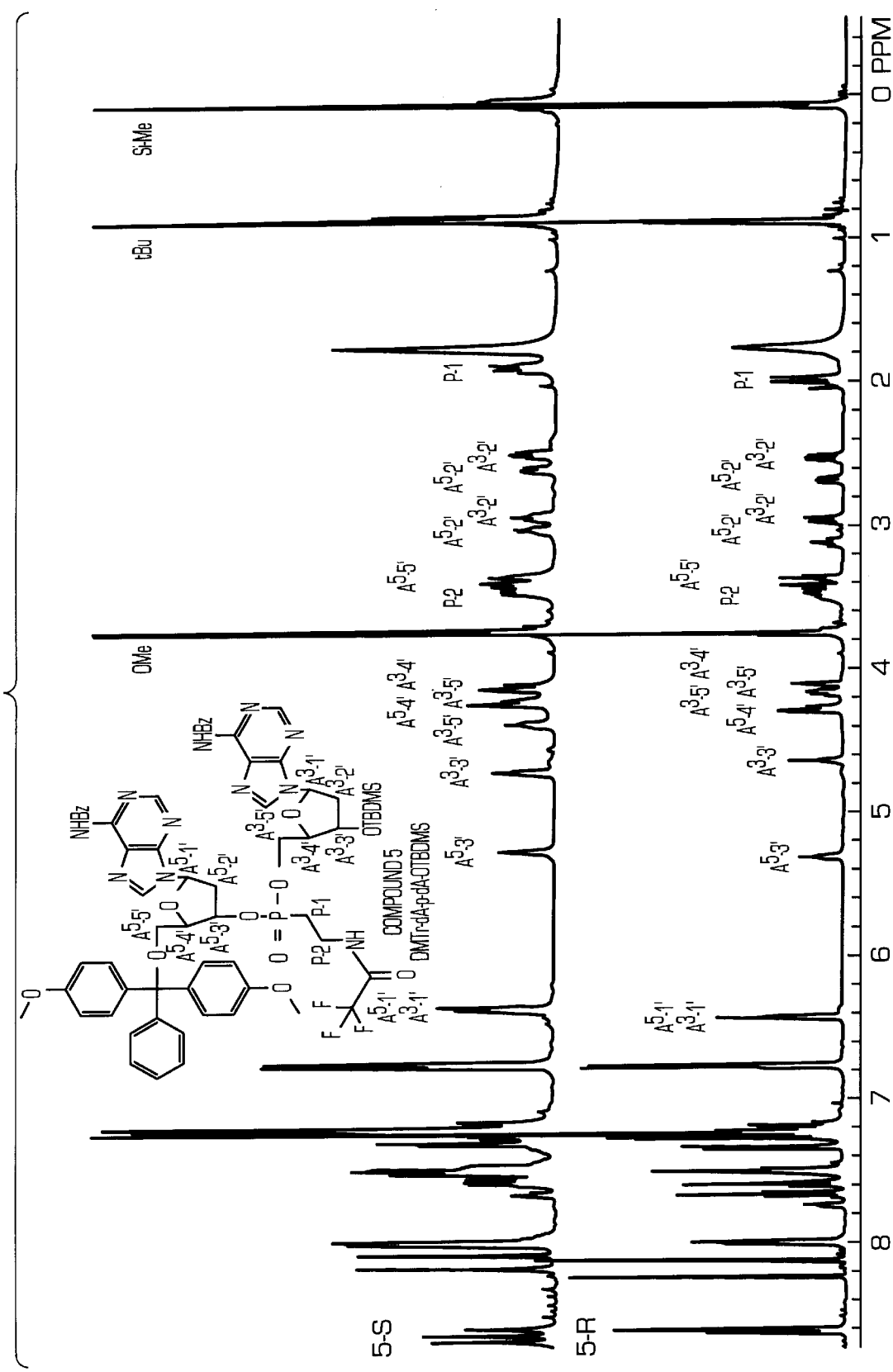

The NMR (CDCl$_3$) charts of Compound 5S ($B_1$=T, $B_2$=$C^{Bz}$, $R_{31}$=TFA, $R_{32}$=TBDMS) and Compound 5R ($B_1$=T, $B_2$=$C^{Bz}$, $R_{31}$=TFA, $R_{32}$=TBDMS) at 500 MHz are shown in FIG. 4. The NMR (CDCl$_3$) charts of Compound 5S ($B_1$=$A^{Bz}$, $B_2$=$A^{Bz}$, $R_{31}$=TFA, $R_{32}$=TBDMS) and Compound 5R ($B_1$=$A^{Bz}$, $B_2$=$A^{Bz}$, $R_{31}$=TFA, $R_2$=TBDMS) at 500 MHz are shown in FIG. 5.

Figure 22:
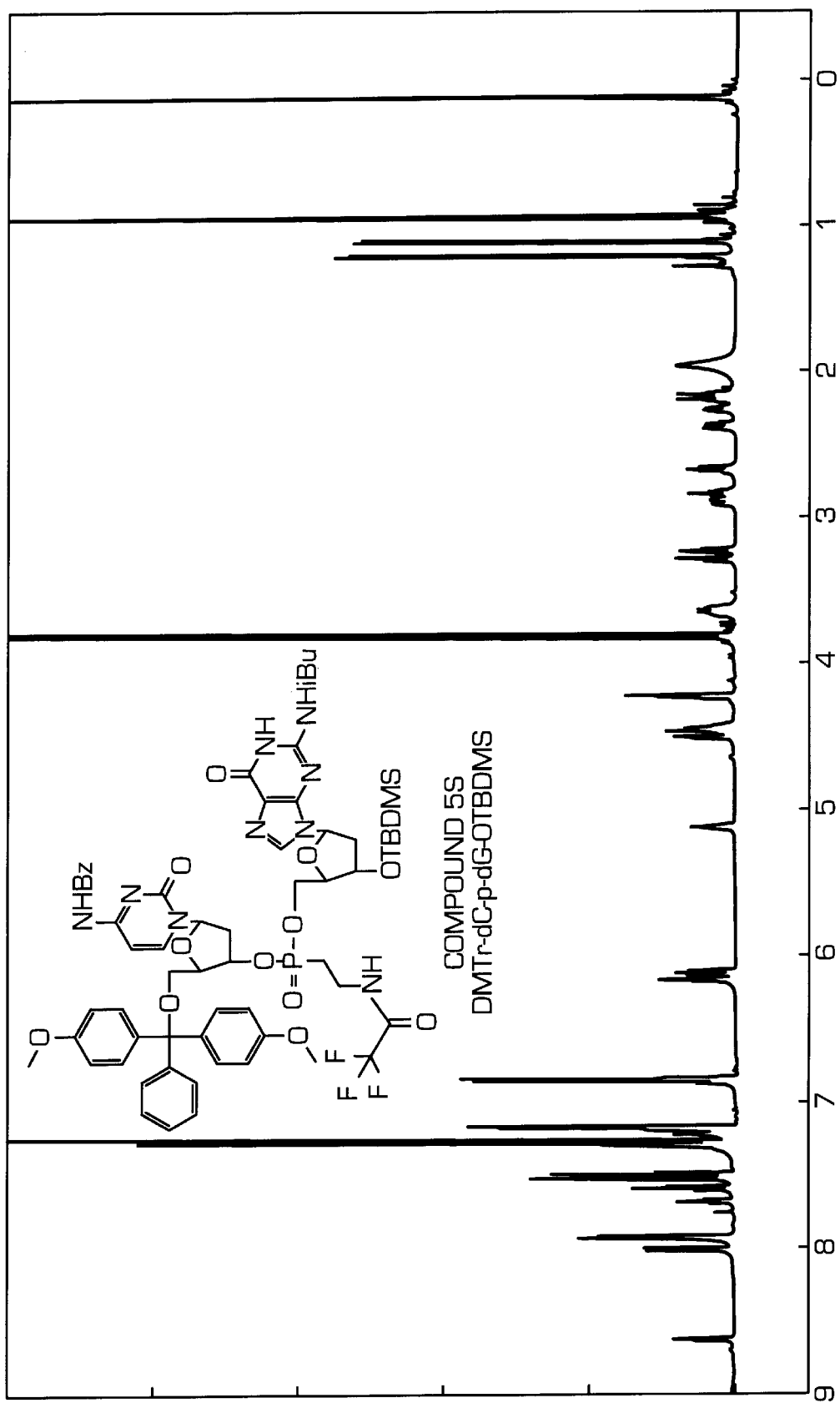
FIG. 22 is the NMR chart of Compound 5S.

The NMR (CDCl$_3$) chart of Compound 5S ($B_1$=$C^{Bz}$, $B_2$=$G^{iBu}$, $R_{31}$=TFA, $R_{32}$=TBDMS) at 500 MHz is shown in FIG. 22.

Figure 23:
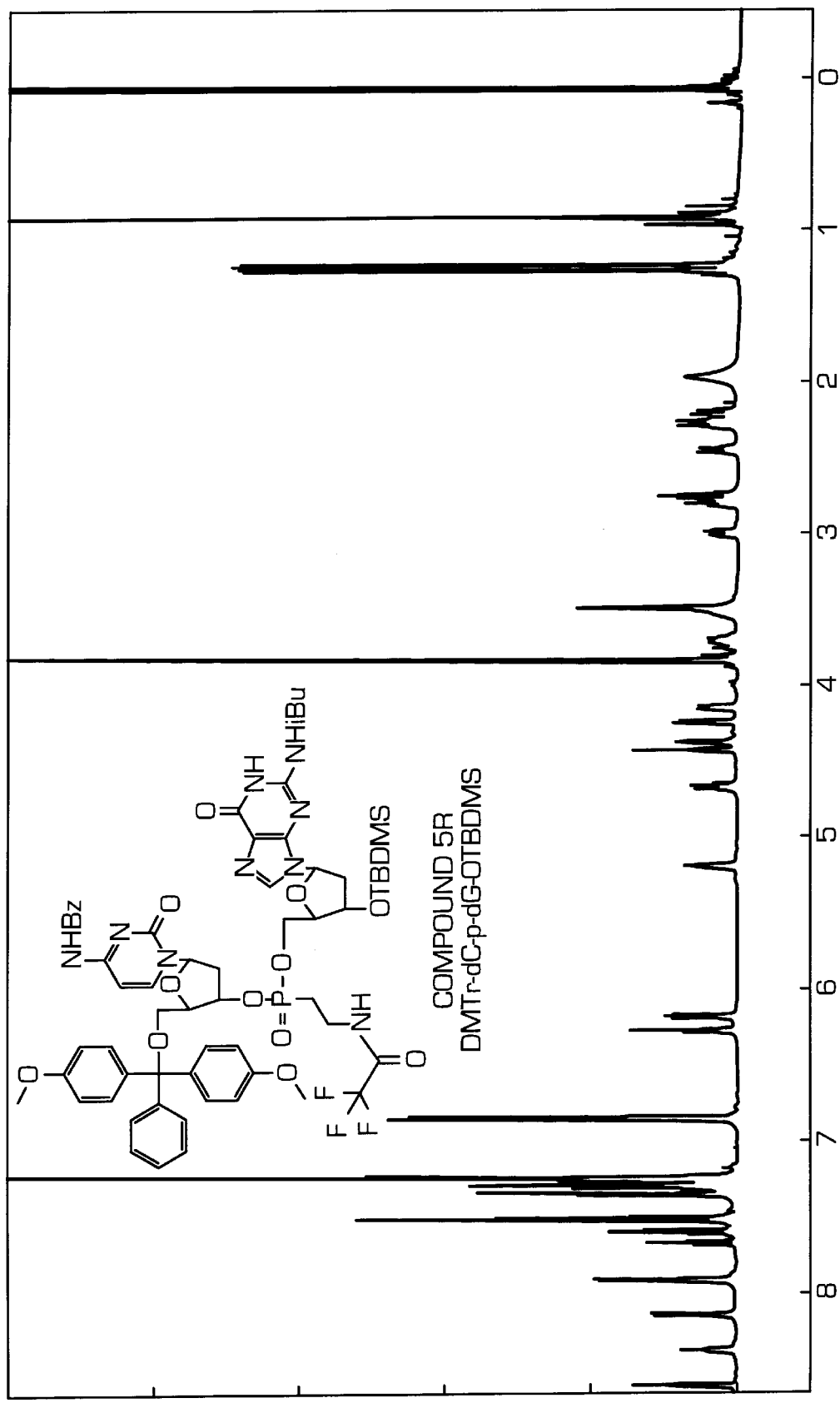
FIG. 23 is the NMR chart of Compound 5R.

The NMR (CDCl$_3$) chart of Compound 5R ($B_1$=$C^{Bz}$, $B_2$=$G^{iBu}$, $R_{31}$=TFA, $R_{32}$=TBDMS) at 500 MHz is shown in FIG. 23.

Figure 6:
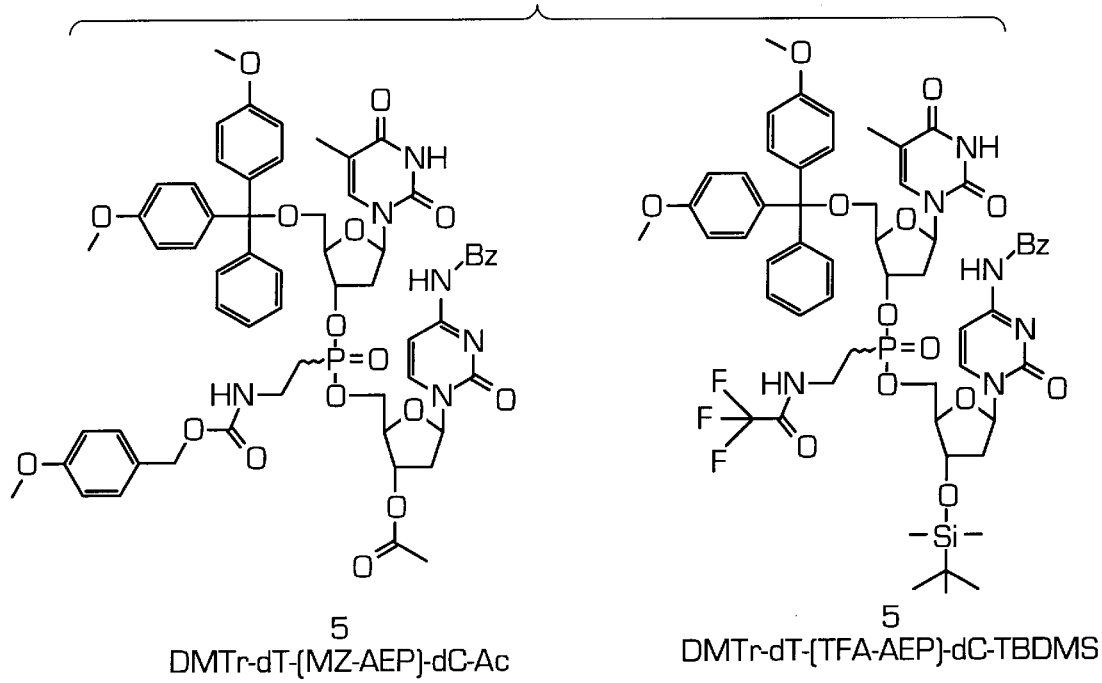

Detailed structures of Compounds 5S/5R ($B_1$=T, $B_2$=$C^{Bz}$, $R_{31}$=MZ, $R_{32}$=Ac) and 5S/5R ($B_1$=T, $B_2$=$C^{Bz}$, $R_{31}$=TFA, $R_{32}$=TBDMS) are shown in FIG. 6. As is evident from Table 2, the difference in rate of migration (Rf) by thin layer chromatography (TLC) between the R- and S-stereoisomers of Compound 5 depends on the kinds of the hydroxyl- and amino-protecting groups ($R_{31}$ and $R_{32}$), and when $R_{31}$=TFA, $R_{32}$=TBDMS, separation of the two stereoisomers are easy. For TLC, a commercial device (Merck Silica gel 60 $F_{254}$

TABLE 3

| Com- pound | $B_1$ | $B_2$ | mol | Reagent | | Com- pound | yield |
|---|---|---|---|---|---|---|---|
| | | | | Bu$_4$NF | TEAA*[1] | | |
| 5S | T | $C^{Bz}$ | 7.7 μmol | 3.0 eq. | — | 6S | 37% |
| 5R | T | $C^{Bz}$ | 2.6 μmol | 1.9 eq. | — | 6R | 37% |
| 5S | $A^{Bz}$ | $A^{Bz}$ | 55.6 μmol | 2.0 eq. | 1.0 eq. | 65 | 48% |
| 5R | $A^{Bz}$ | $A^{Bz}$ | 51.8 μmol | 2.0 eq. | 1.0 eq. | 6R | 58% |
| 5S | $C^{Bz}$ | $G^{iBu}$ | 178 μmol | 6.0 eq. | 1.0 eq. | 6S | 50% |
| 5R | $C^{Bz}$ | $G^{iBu}$ | 269 μmol | 3.0 eq. | 1.0 eq. | 6R | 48% |

*[1] TEAA: Triethylamine-acetate Buffer (pH 7.0)

EXAMPLE 4

Figure 9:
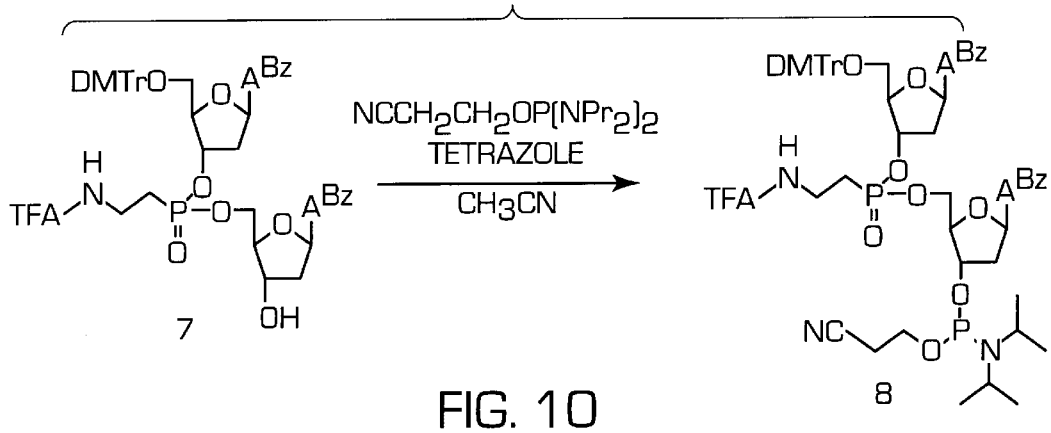

As shown in FIG. 9, Compound 7 was phosphoroamidited in accordance with the method disclosed in Nucleic Acid Research, vol.14, 7391, to give Compound 8, which was subsequently used for synthesis of a DNA oligomer by a DNA synthesizer without isolation.

EXAMPLE 5

Figure 10:
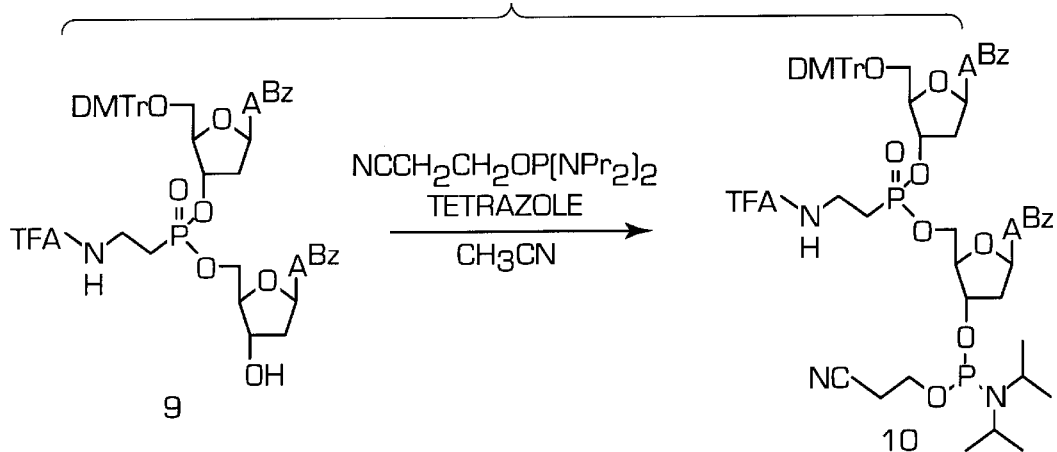

As shown in FIG. 10, Compound 9 was phosphoroamidited in the same manner as in Example 4 to give Compound 10, which was subsequently used for synthesis of a DNA oligomer by a DNA synthesizer without isolation.

EXAMPLE 6

A DNA oligomer A-13S having the following base sequence was synthesized by using Compound 8 and adenosine 3'-phosphoroamidite as starting materials by a DNA synthesizer (Applied Biosystems Model 380B DNA Synthesizer, manufactured by Perkin-Elmer).

A-13S: (5')AAAAA*AAAAAAAA(3')(SEQ ID NO:1)

wherein "*" indicates the location of the phosphonic diester attributed to Compound 8.

EXAMPLE 7

A DNA oligomer A-13R having the following base sequence was synthesized by using Compound 10 and adenosine 3'-phosphoroamidite as starting materials by a DNA synthesizer (Applied Biosystems Model 380B DNA Synthesizer, manufactured by Perkin-Elmer).

A-13R: (5')AAAAA*AAAAAAAA(3')(SEQ ID NO:1)

wherein "*" indicates the location of the phosphonic diester attributed to Compound 10.

EXAMPLE 8

Figure 11:
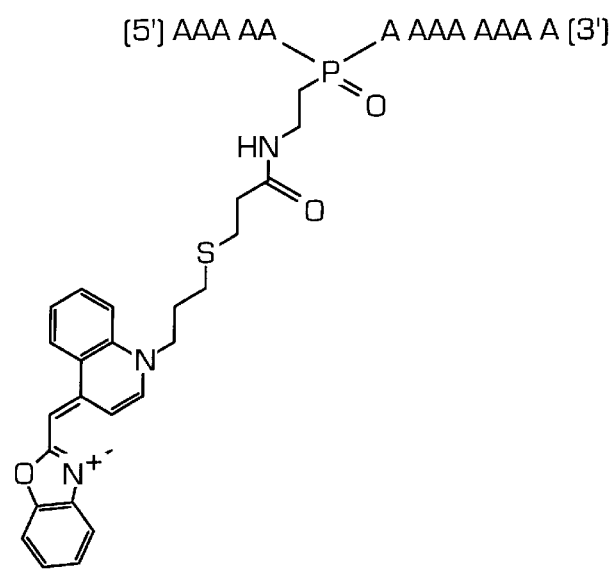

A DNA probe YOA-13S shown in FIG. 11 was obtained by using DNA oligomer A-13S as a starting material in accordance with the method disclosed in U.S. Pat. No. 5,814,447 or EP 714986.

Figure 12:
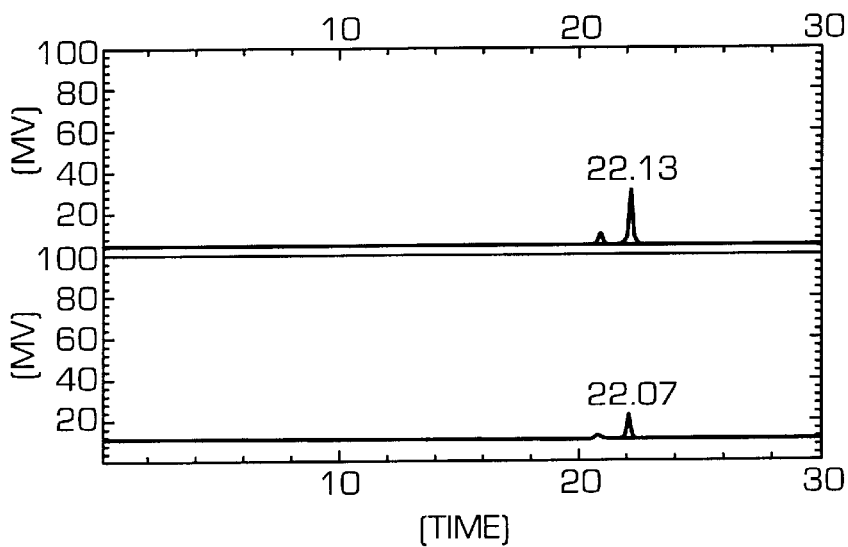

The HPLC chart of purified YOA-13S was shown in FIG. 12.

EXAMPLE 9

Figure 13:
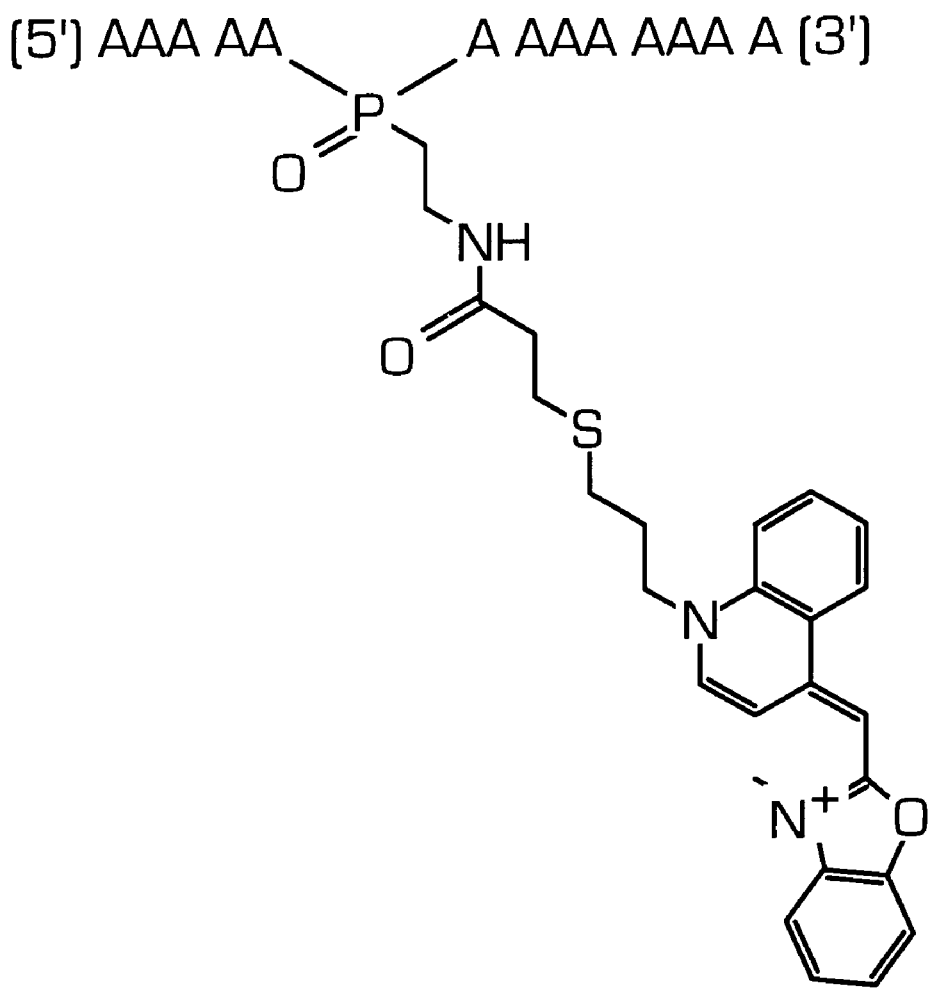

A DNA probe YOA-13R shown in FIG. 13 was obtained by using DNA oligomer A-13R as a starting material in accordance with the method disclosed in U.S. Pat. No. 5,814,447 or EP 714986.

Figure 14:
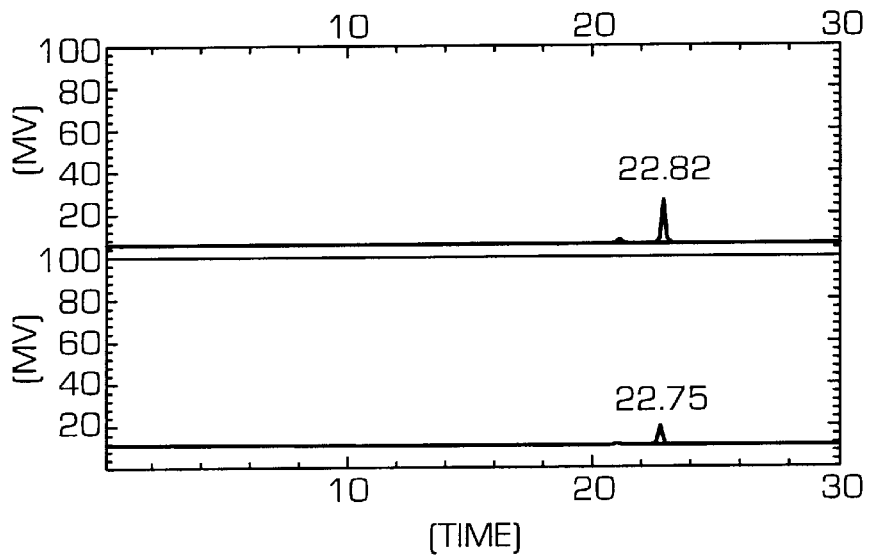

The HPLC chart of purified YOA-13R was shown in FIG. 14.

EXAMPLE 10

Figure 15:
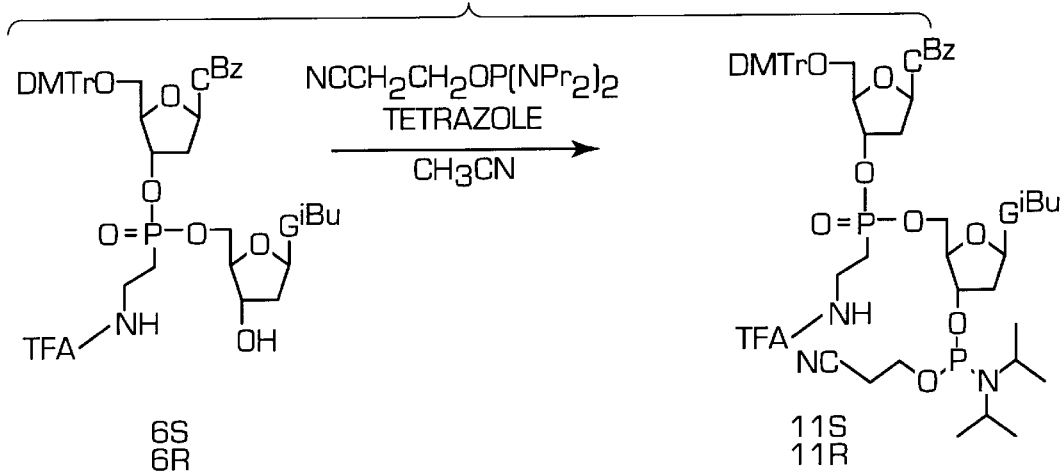

As shown in FIG. 15, Compound 6S (wherein $B_1=C^{Bz}$, $B_2=G^{iBu}$) prepared in Example 3 was treated in the same manner as in Example 4 to give Compound 11S, which was subsequently used for synthesis of a DNA oligomer without isolation.

EXAMPLE 11

As shown in FIG. 15, Compound 6R (wherein $B_1=C^{Bz}$, $B_2=G^{iBu}$) prepared in Example 3 was treated in the same manner as in Example 4 to give Compound 11R, which was subsequently used for synthesis of a DNA oligomer without isolation.

EXAMPLE 12

A DNA oligomer 271S having the following base sequence (wherein "*" indicates the location of the phosphonic diester attributed to Compound 11S) was synthesized by using Compound 11S prepared in Example 10 and G, C and T-phosphoroamidites as starting materials in the same manner as in Example 6.

271S: (5')CTCGC*GGGGGCTG(3')(SEQ ID NO:2)

EXAMPLE 13

A DNA oligomer 271R having the following base sequence (wherein "*" indicates the location of the phosphonic diester attributed to Compound 11R) was synthesized by using Compound 11R prepared in Example 11 and G, C and T-phosphoroamidites as starting materials in the same manner as in Example 6.

271R: (5')CTCGC*GGGGGCTG(3')(SEQ ID NO:2)

EXAMPLE 14

Figure 16:
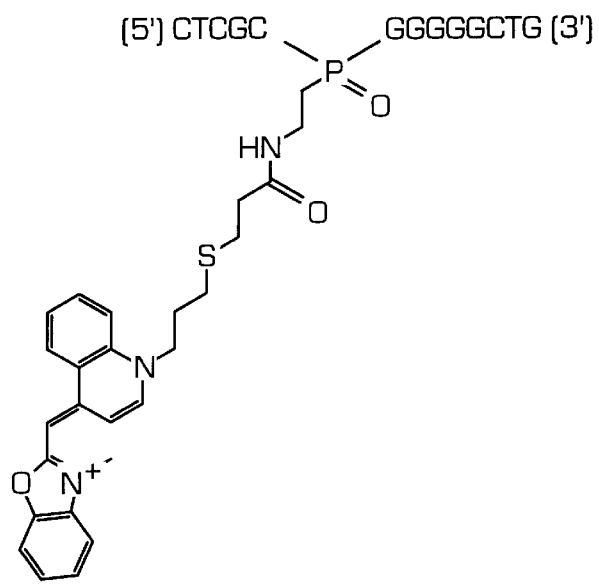
Figure 17:
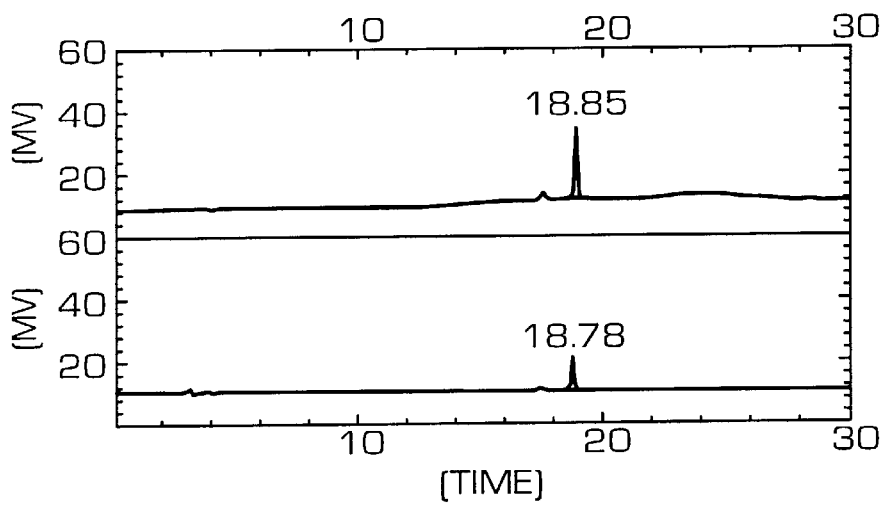

A DNA probe YO-271S shown in FIG. 16 was obtained by using DNA oligomer 271S as a starting material in the same manner as in Example 8. The HPLC chart of purified YO-271S was shown in FIG. 17.

EXAMPLE 15

Figure 18:
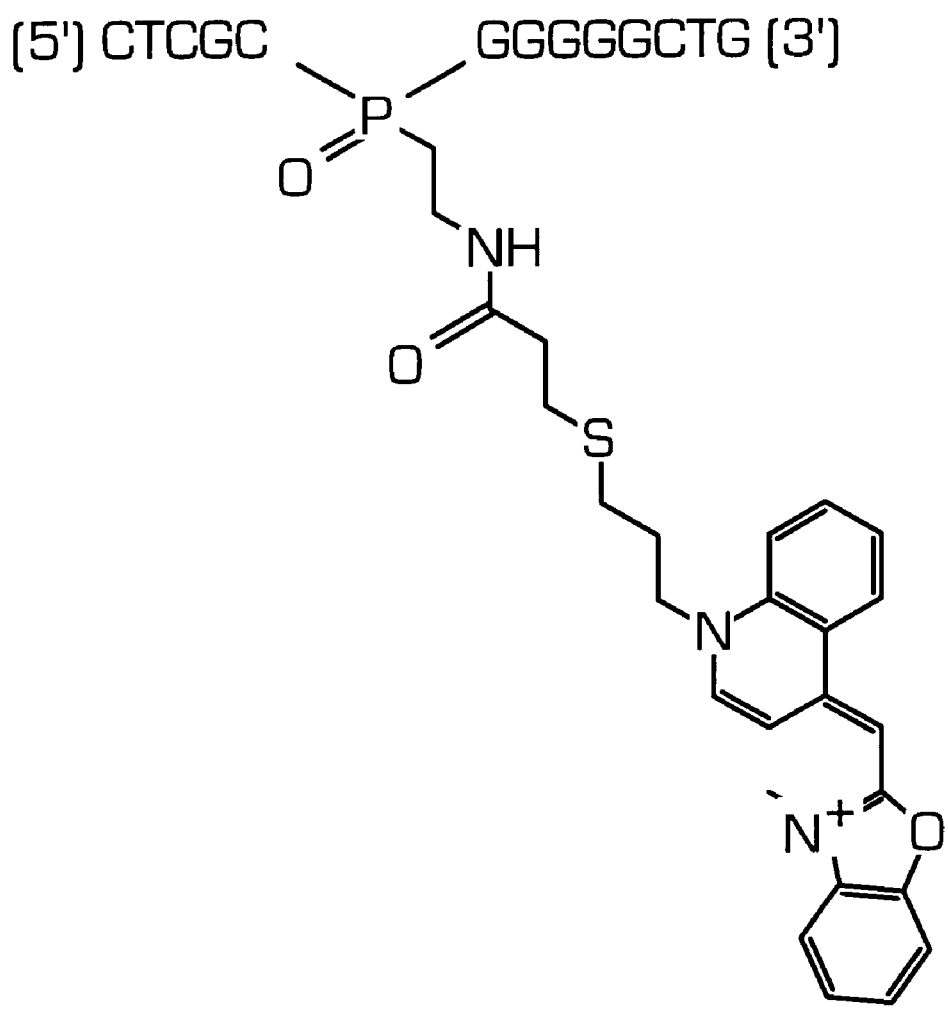
Figure 19:
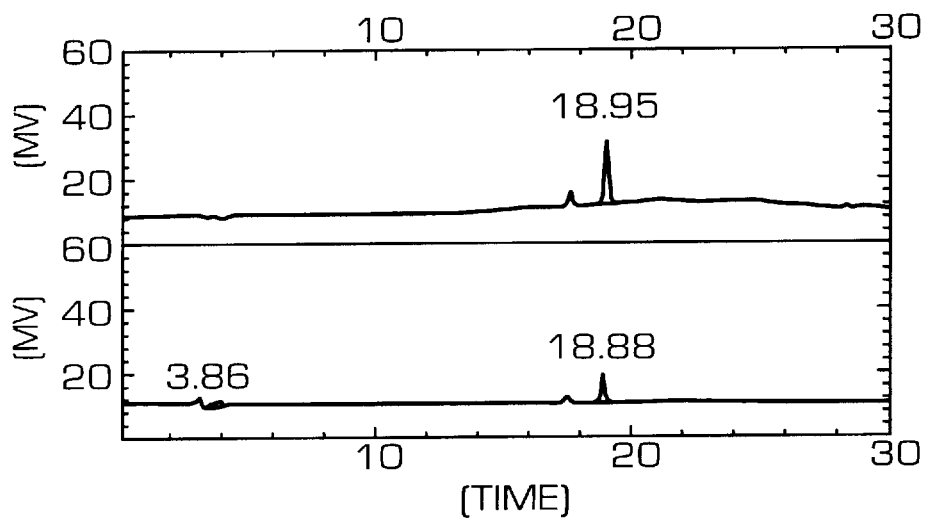

A DNA probe YO-271R shown in FIG. 18 was obtained by using DNA oligomer 271R as a starting material in the same manner as in Example 8. The HPLC chart of purified YO-271S was shown in FIG. 19.

EXAMPLE 16

A target nucleic acid was detected with the DNA probes (YO-A13R and YO-A13S) prepared in Examples 8 and 9 as follows.

Method

① To a hybridization buffer (1×SSC, 1 mM EDTA) containing a probe (YO-A13R or YO-A13S; final concentration 10 nM), target DNA (oligo-dT (30 mer), oligo-dA (30 mer) or a recombinant HCV RNA; final concentration 10 nM, respectively) was added, and the resulting reaction solution was pipetted into a fluorometric cuvette.

② The fluorescence spectrum of the reaction solution was measured by means of a fluorescence spectrometer FP-777 (JASCO Corporation) (excitation wavelength 490 nm/HW 5 nm).

Results

Figure 20:
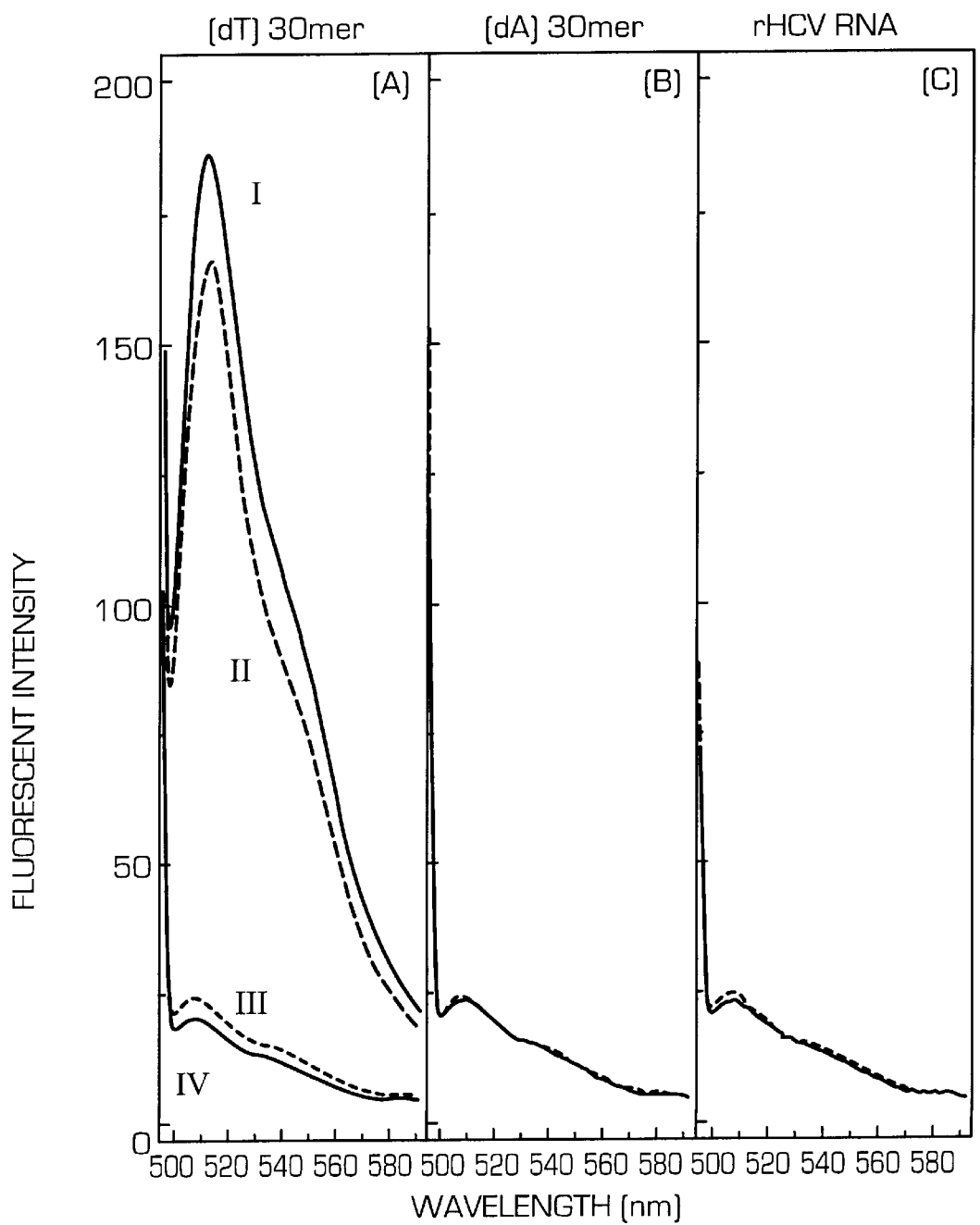

The fluorescence spectra thus obtained are shown in FIG. 20.

(A) I YO-A13S (10 nM) and oligo-dT (30 mer) (10 nM)
II YO-A13R (10 nM) and oligo-dT (30 mer) (10 nM)
III YO-A13R (10 nM) alone
IV YO-A13S (10 nM) alone (B) (—) YO-A13S (10 nM) and oligo-dA (30 mer) (10 nM)
(- - -) YO-A13R (10 nM) and oligo-dA (30 mer) (10 nM)

(C) (—) YO-A13S (10 nM) and recombinant HCV RNA (10 nM)
(- - -) YO-A13R (10 nM) and recombinant HCV RNA (10 nM)

Both YO-A13R and YO-A13S showed remarkable fluorescence enhancement in the presence of the complementary oligo-dT (30 mer) (FIG. 20 (A)). In contrast, the fluorescence intensity in the presence of uncomplementary nucleic acids, oligo-dA (30 mer) and rHCV RNA, was comparable with that in the case of the probe only.

EXAMPLE 17

The melting points of the DNA probes (YO-A13R and YO-A13S) prepared in Examples 8 and 9 were measured as follows.

Method

① A DNA probe (YO-A13R or YO-A13S) or dA (13 mer) (final concentration 1.5 μM, respectively) was added to a hybridization buffer (1×SSC, 1 mM EDTA) containing a target nucleic acid, dT (30 mer).

② The reaction solution was gradually cooled from 90° C. to 25° C. with monitoring of the temperature while the UV absorption was measured at 260 nm.

Results

Tm values

YO-A13R: 47° C.

YO-A13S: 47° C.

Oligo-dA (13 mer): 37° C.

The Tm of the two probes were 10° C. higher than that of oligo-dA (13 mer) which was not modified with YO, which indicates stabilization of double-stranded DNA formed by the probes upon intercalation of the YO molecule. The fluorescence enhancement by the probes observed in Example 16 is supposed to be attributable to the intercalation.

EXAMPLE 18

A target nucleic acid was detected with the DNA probes (YO-271R and YO-271S) prepared in Examples 14 and 15 as follows.

Method

① To a hybridization buffer (1×SSC, 1 mM EDTA) containing a probe (YO-271R or YO-271S; final concentration 25 nM), a target DNA, Temp271, (final concentration 25 nM) was added, and the resulting reaction solution was pipetted into a fluorometric cuvette.

② The fluorescence spectrum of the reaction solution was measured by means of a fluorescence spectrometer FP-777 (JASCO Corporation) (excitation wavelength 490 nm/HW 5 nm, temperature: 37° C.).

Results

Figure 21:
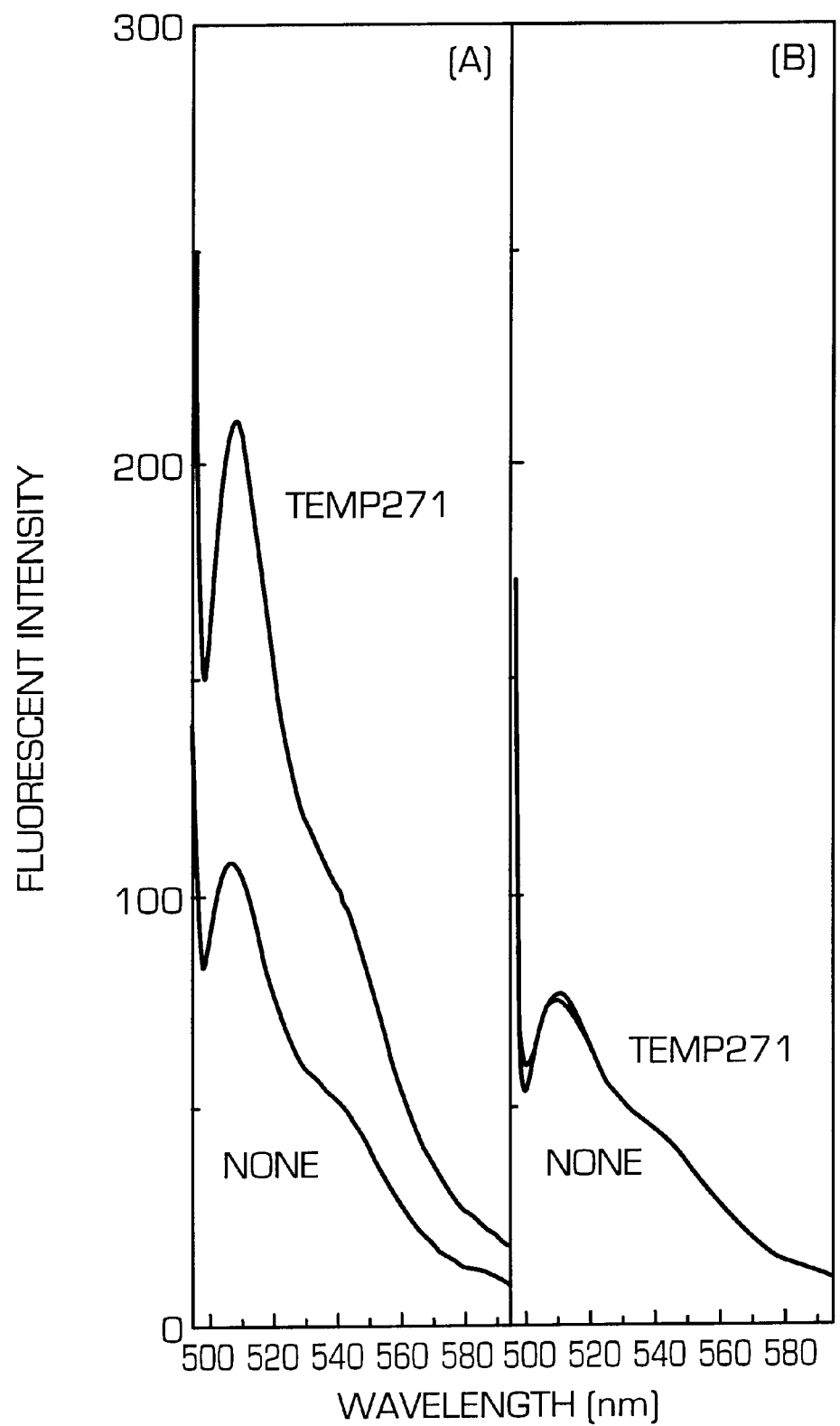

The fluorescence spectra thus obtained are shown in FIG. 21.

(A) Temp271: YO-271S (25 nM) and Temp271 (25 nM)
None: YO-271S alone (B) Temp271: YO-271R (25 nM) and Temp271 (25 nM)
None: YO-271R alone YO-271S showed remarkable fluorescence enhancement in the presence of complementary Temp271, while fluorescence intensity of YO-271R in the presence of complementary Temp271 was comparable with that in the case of the probe only.

EXAMPLE 19

The melting points of the DNA probes (YO-271R and YO-271S) prepared in Examples 14 and 15 were measured as follows.

Method

DNA271: (5')CTCGCGGGGGCTG(3')(SEQ ID NO:3)

Temp271: (5')GTGCCCCCGCGAG(3')(SEQ ID NO:4)

① A DNA probe (YO-271R or YO-271S) or a synthetic oligomer DNA271 (final concentration 1.0 μM, respectively) was added to a hybridization buffer (1×SSC, 1 mM EDTA) containing a target nucleic acid, Temp271.

② The reaction solution was gradually cooled from 90° C. to 25° C. with monitoring of the temperature while the UV absorption was measured at 260 nm.

Results

Tm values

YO-271R: 62° C.

YO-271S: 66° C.

DNA271: 59° C.

The Tm of the probe YO-271S, which showed fluorescence enhancement in Example 18, was higher than that of DNA271 which was not modified with YO. On the other hand, the Tm of YO-271R, which did not show fluorescence enhancement, was not much different from that of DNA271. These results indicate stabilization of double-stranded DNA formed by the probe YO-271S upon saturated aqueous sodium chloride and extracted with 10 ml of chloroform three times. The organic layers were combined and dried over magnesium sulfate, and the solvent was removed by evaporation in vacuo. Purification of the residue by silica gel column chromatography gave 1 mg of Compound 14 in FIG. 24 in a 37% yield.

EXAMPLE 21

Figure 24:
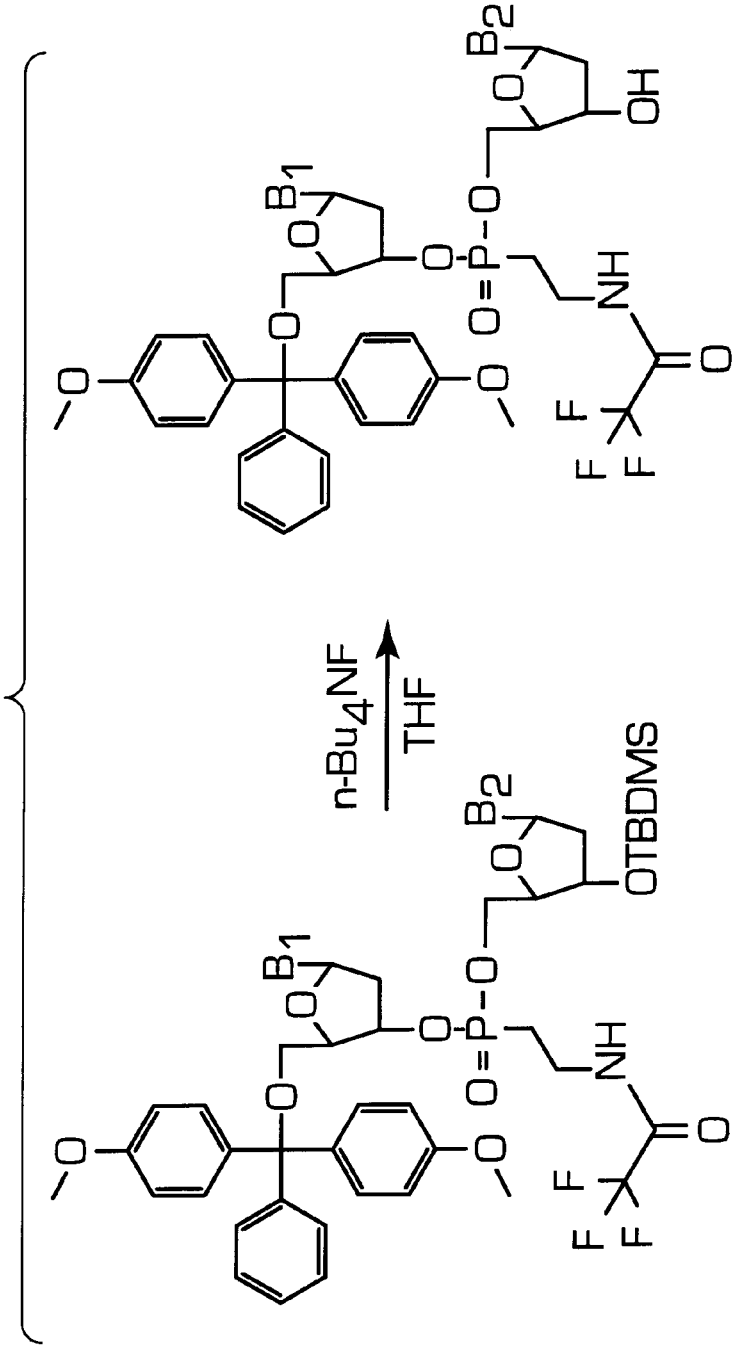
FIG. 24 illustrates the substrates and the reaction products of the reactions in Examples 20 to 22.

To Compound 13 in FIG. 24 (73 mg, 55.6 μmol) in 4.5 ml of THF, 2M triethylamine-acetate buffer (27.8 μl, pH 7.0) was added dropwise, and then 0.1M Bu$_4$NF in THF (1.11 ml) was added dropwise. After 1 hours, the reaction solution was diluted with saturated aqueous sodium chloride and extracted with 10 ml of chloroform three times. The organic layers were combined and dried over magnesium sulfate, and the solvent was removed by evaporation in vacuo. Purification of the residue by silica gel column chromatography gave 32 mg of Compound 15 in FIG. 24 in a 48% yield.

EXAMPLE 22

To Compound 13 in FIG. 24 (68 mg, 51.8 μmol) in 4.1 ml of THF, THF (1.08 ml) containing 0.1M Bu$_4$NF and 0.05M triethylamine-acetate buffer was added dropwise. After 2 hours of stirring, the reaction solution was diluted with saturated aqueous sodium chloride and extracted with 10 ml of chloroform three times. The organic layers were combined and dried over magnesium intercalation of the YO molecule. The remarkable fluorescence enhancement observed only for YO-271S is supposed to be attributable to the intercalation.

EXAMPLE 20

To Compound 12 in FIG. 24 (15 mg, 12.8 μmol) in 2.3 ml of THF, 2M triethylamine-acetate buffer (6.4 μl, pH 7.0) was added dropwise, and then 0.1M Bu$_4$NF in THF (0.255 ml) was added dropwise. After 2 hours, the reaction solution was diluted with saturated aqueous sodium chloride and extracted with 10 ml of chloroform three times. The organic layers were combined and dried over magnesium sulfate, and the solvent was removed by evaporation in vacuo. Purification of the residue by silica gel column chromatography gave 7 mg of Compound 14 in FIG. 24 in a 52% yield. For comparison, to Compound 12 in FIG. 24 (9 mg, 7.7 μmol) in 1.0 ml of THF, 0.1M Bu$_4$NF in THF (23 μl) was added dropwise. After 6 hours, the reaction solution was diluted with saturated aqueous sodium chloride and extracted with 10 ml of chloroform three times. The organic layers were combined and dried over magnesium sulfate, and the solvent was removed by evaporation in vacuo. Purification of the residue by silica gel column chromatography gave 3 mg of Compound 14 in FIG. 24 in a 37% yield. For another comparison, to Compound 12 in FIG. 24 (3 mg, 2.6 μmol) in 0.05 ml of THF, 0.1M Bu$_4$NF in THF (50 μl) was added dropwise. After 3.5 hours, the reaction solution was diluted with sulfate, and the solvent was removed by evaporation in vacuo. Purification of the residue by silica gel column chromatography gave 36 mg of Compound 15 in FIG. 24 in a 58% yield.

The results of Examples 20 to 22 described above are shown in Table 4. As is evident from Table 4, addition of acetic acid and triethylamine at the time of the TBDMS-eliminating reaction using tetrabutylammonium fluoride improves the yield by nearly 20%, supposedly because acetic acid and triethylamine moderated the acidity and basicity of the reagent tetrabutylammonium fluoride and thereby suppressed production of decomposition products.

TABLE 4

| | Substrate | Solvent | Reagent | yield |
|---|---|---|---|---|
| Example 20 | Compound 12 | THF + TEAA Buffer (1.0 eq.) | 0.1 M Bu$_4$NF (2.0 eq.)/THF | 52% |
| | Compound 12 | THF | 1.0 M Bu$_4$NF (3.0 eq.)/THF | 37% |
| | Compound 12 | THF | 0.1 M Bu$_4$NF (1.9 eq.)/THF | 37% |
| Example 21 | Compound 13 | THF + TEAA Buffer (1.0 eq.) | 0.1 M Bu$_4$NF (2.0 eq.)/THF | 48% |
| Example 22 | Compound 13 | THF | (0.1 M Bu$_4$NF (2.0 eq.) + 0.05 M TEAA (1.0 eq.)/THF | 58% |

TEAA Buffer: Triethylamine-acetate buffer

According to the present invention, it is possible to obtain a nucleic acid probe having an intercalator as a label attached in the middle of the nucleic acid sequence via an aminoalkylphosphonate linker. Especially, it is reported for the first time that it is possible to obtain a nucleic acid probe having a configurationally different phosphorus atom by utilizing the difference in Rf.

What is claimed is:

1. An optically active DNA probe of formula (1),

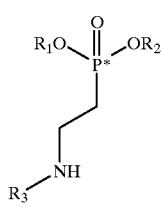
(1)

wherein P* is an optically active phosphorus atom, each of $R_1$ and $R_2$ is a DNA oligomer having a desired nucleotide sequence, and $R_3$ is a fluorescent intercalative dye attached via a linker, wherein said probe has an optically active configuration about P*.

2. The DNA probe according to claim 1, wherein said probe has a R- or S-configuration about P*.

3. The DNA probe according to claim 1, wherein a fluorescence characteristic of the fluorescent intercalative dye chances when the dye is intercalated into a complementary binding portion between a target nucleotide molecule and the DNA probe.

4. An optically active DNA oligomer of formula (2),

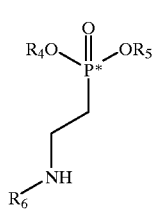
(2)

wherein P* is an optically active phosphorus atom, each of $R_4$ and $R_5$ is a DNA oligomer having a desired nucleotide sequence, and $R_6$ is a hydrogen atom or an amino-protecting group, and wherein said probe has an optically active configuration about P*.

5. The DNA oligomer according to claim 4, wherein said probe has a R- or S-configuration about P*.

6. A method of preparing an optically active DNA comprising attaching a fluorescent intercalative dye to the nitrogen atom in the aminoethylphosphonate of the optically active DNA oligomer of formula (2) via a linker,

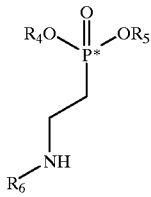
(2)

wherein P* is an optically active phosphorus atom, each of $R_4$ and $R_5$ is a DNA oligomer having a desired nucleotide sequence, and $R_6$ is a hydrogen atom or an amino-protecting group, having an optically active configuration about P*.

7. A method of preparing an optically active DNA oligomer comprising the steps of:

(A) reacting an optically active dinucleotide of formula (4),

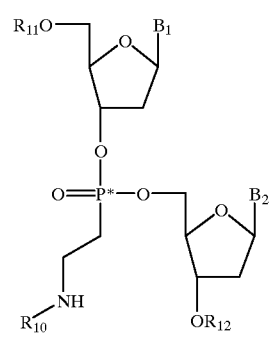
(4)

wherein P* is an optically active phosphorus atom, $B_1$ and $B_2$ are desired nucleotide bases, $R_{10}$ is an amino-protecting group, $R_{11}$ is a hydroxyl-protecting group, and $R_{12}$ is a hydroxyl-protecting group, a hydrogen atom, a phosphate group or a phosphoroamidite group, with the 5'-hydroxyl group of a first DNA oligomer having a desired nucleotide sequence; and then (B) reacting a second DNA oligomer having a desired nucleotide sequence to the 5'-terminal.

8. A method of preparing an optically active dinucleotide of formula (8), (8)

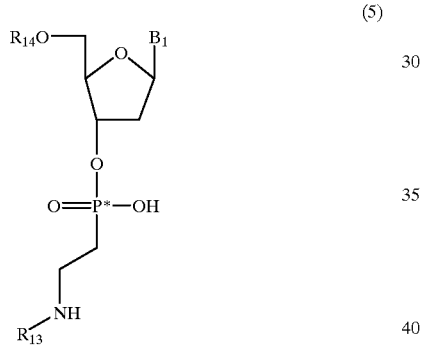

wherein P* is an optically active phosphorus atom, $B_1$ and $B_2$ are desired nucleotide bases, $R_{16}$ is an amino-protecting group, $R_{17}$ is a hydroxyl-protecting group, and $R_{18}$ is a t-butyldimethylsilyl group, which comprises the steps of:

(A) reacting a phosphonic nucleotide of formula (5), (5)

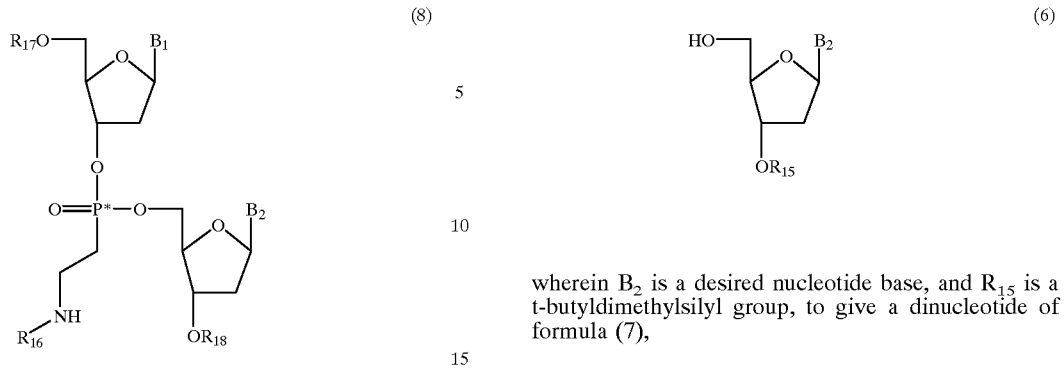

wherein $B_1$ is a desired nucleotide base, $R_{13}$ is an amino-protecting group, and $R_{14}$ is a hydroxyl-protecting group, with a nucleoside of formula (6), (6)

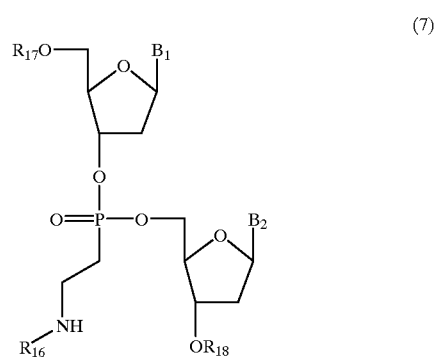

wherein $B_2$ is a desired nucleotide base, and $R_{15}$ is a t-butyldimethylsilyl group, to give a dinucleotide of formula (7), (7)

wherein each of $B_1$ and $B_2$ is a desired nucleotide base, $R_{16}$ is an amino-protecting group, $R_{17}$ is a hydroxyl-protecting group, and $R_{18}$ is a t-butyldimethylsilyl group; and (B) optically resolving the resulting dinucleotide.

9. The optically active DNA probe of claim 1, wherein the linker comprises an aminoalkylphosphate.

10. The method of claim 6, wherein the linker comprises an aminoalkylphosphate.

11. The method of claim 7, wherein the amino protecting group is a trifluoroacetyl (TFA) group and a protecting group at the 3' position at $R_{12}$ is a phosphoroamidite group.

12. The method of claim 8, wherein the amino protecting group is a trifluoroacetyl (TFA) group.

* * * * *